(12) United States Patent
Griebenow et al.

(10) Patent No.: US 7,662,956 B2
(45) Date of Patent: Feb. 16, 2010

(54) TETRAHYDROBENZO[D]AZEPIN-2-ONE DERIVATIVES AND THE USE THEREOF FOR TREATING CARDIOVASCULAR DISEASES

(75) Inventors: Nils Griebenow, Dormagen (DE); Timo Flessner, Wuppertal (DE); Michael Härter, Leverkusen (DE); Martin Raabe, Ulm (DE); Anja Buchmüller, Essen (DE); Hilmar Bischoff, Wuppertal (DE); Peter Ellinghaus, Wuppertal (DE); Peter Kolkhof, Wuppertal (DE)

(73) Assignee: Bayer Shering Pharma AG, Leverkusen (DE)

( * ) Notice: Subject to any disclaimer, the term of this patent is extended or adjusted under 35 U.S.C. 154(b) by 0 days.

(21) Appl. No.: 10/588,862

(22) PCT Filed: Feb. 1, 2005

(86) PCT No.: PCT/EP2005/000960

§ 371 (c)(1),
(2), (4) Date: Jun. 19, 2007

(87) PCT Pub. No.: WO2005/077907

PCT Pub. Date: Aug. 25, 2005

(65) Prior Publication Data

US 2007/0287698 A1 Dec. 13, 2007

(30) Foreign Application Priority Data

Feb. 10, 2004 (DE) .................. 10 2004 006 325

(51) Int. Cl.
*C07D 233/16* (2006.01)
*A61K 31/55* (2006.01)

(52) U.S. Cl. .............. 540/595; 514/212.07; 514/212.08

(58) Field of Classification Search ............ 514/212.07; 540/595
See application file for complete search history.

(56) References Cited

U.S. PATENT DOCUMENTS 6,537,987 B1 3/2003 Hamanaka et al.
2003/0078251 A1 4/2003 Kori et al.

FOREIGN PATENT DOCUMENTS

WO WO 97/48701 * 12/1997
WO WO 02/057258 A 7/2002

OTHER PUBLICATIONS

Morissette et al. Advanced Drug Delivery Reviews 2004, 56, 275-300.*
Vippagunta, Sudha R. "Crystalline Solids." Advanced Drug Delivery Reviews 48(2001): 3-26.*
Pandit et al. Journal of Biological Chemistry, "Crystal Structure of Human Squalene Synthase" vol. 275(39) 2000, 30610-30617.*
G. Assmann et al.: "The Münster Heart Study (PROCAM)," European Heart Journal, vol. 19, Supp. A., 1998, pp. A2-A11.
N. S. Watson et al.: "7 Squalene Synthase Inhibitors: Their Potential as Hypocholesterolaemic Agents," Progress in Medicinal Chemistry, vol. 33, 1996, pp. 331-378.
H. Hiyoshi et al.: "Squalene Synthase Inhibitors Reduce Plasma Triglyceride Through a Low-Density Lipoprotein Receptor-Independent Mechanism," European Journal of Pharmacology, vol. 431, 2001, pp. 345-352.

* cited by examiner

*Primary Examiner*—Sharmila Gollamudi Landau
*Assistant Examiner*—Kortney L Klinkel
(74) *Attorney, Agent, or Firm*—Edwards Angell Palmer & Dodge LLP; Barry Kramer; Ralph A. Loren

(57) ABSTRACT

The present application relates to novel tetrahydrobenzo[d]azepin-2-one derivatives, processes for their preparation, their use for the treatment and/or prophylaxis of diseases, and their use for producing medicaments for the treatment and/or prophylaxis of diseases, preferably for the treatment and/or prevention of cardiovascular disorders, especially of dyslipidaemias, arteriosclerosis, restenosis and ischaemias.

6 Claims, No Drawings

TETRAHYDROBENZO[D]AZEPIN-2-ONE DERIVATIVES AND THE USE THEREOF FOR TREATING CARDIOVASCULAR DISEASES

The present application relates to novel tetrahydrobenzo[d]azepin-2-one derivatives, processes for their preparation, their use for the treatment and/or prophylaxis of diseases, and their use for producing medicaments for the treatment and/or prophylaxis of diseases, preferably for the treatment and/or prevention of cardiovascular disorders, especially of dyslipidaemias, arteriosclerosis, restenosis and ischaemias.

A large number of epidemiological studies has shown a causal connection between dyslipidaemias and cardiovascular disorders. Elevated plasma cholesterol in isolation is one of the greatest risk factors for cardiovascular disorders such as, for example, arteriosclerosis. This relates both to an isolated hypercholesterolaemia and to hypercholesterolaemias combined with, for example, elevated plasma triglycerides or low plasma HDL-cholesterol. Substances which have a cholesterol- or combined cholesterol- and triglyceride-lowering effect ought therefore to be suitable for the treatment and prevention of cardiovascular disorders.

It has already been shown in animal models that plasma cholesterol and triglycerides are lowered by squalene synthase inhibitors. Squalene synthase (EC 2.5.1.21) catalyses the conversion, by reductive condensation, of farnesyl pyrophosphate into squalene. This is a crucial step in cholesterol biosynthesis. Whereas farnesyl pyrophosphate and precursors are also of importance for other cellular metabolic pathways and reactions, squalene serves exclusively as precursor for cholesterol. Inhibition of squalene synthase thus leads directly to a reduction in cholesterol biosynthesis and thus to a fall in plasma cholesterol levels. It has additionally been shown that squalene synthase inhibitors also reduce plasma triglyceride levels. Inhibitors of squalene synthase might thus be employed for the treatment and/or prevention of cardiovascular disorders such as, for example, dyslipidaemias, arteriosclerosis, ischaemia/reperfusion, restenosis and arterial inflammations [cf., for example, Eur. Heart J. 19 (Suppl. A), A2-A11 (1998); Prog. Med. Chem. 33, 331-378 (1996); Europ. J. Pharm. 431, 345-352 (2001)].

It was an object of the present invention to provide novel compounds which can be employed as squalene synthase inhibitors for the treatment and/or prevention in particular of cardiovascular disorders.

WO 02/057258 describes tetrahydrobenzo[d]azepin-2-one derivatives as farnesyltransferase inhibitors for the treatment of cancers, restenosis and neurofibromatosis.

The present invention relates to compounds of the general formula (I)

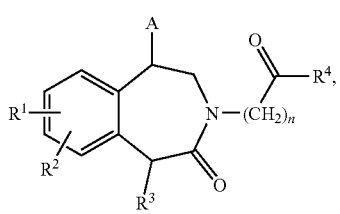

(I)

in which

A is $(C_6-C_{10})$-aryl or 5- to 10-membered heteroaryl, each of which may be substituted up to three times, identically or differently, by substituents selected from the group of halogen, cyano, nitro, trifluoromethyl, trifluoromethoxy, $(C_1-C_6)$-alkyl, $(C_2-C_6)$-alkynyl and $(C_1-C_6)$-alkoxy, or is a group of the formula

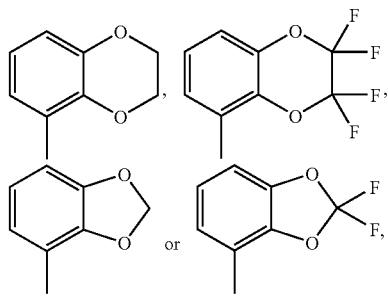

n is the number 1, 2 or 3, $R^1$ and $R^2$ are identical or different and are independently of one another hydrogen, halogen, cyano, nitro, trifluoromethyl, trifluoromethoxy, $(C_1-C_6)$-alkyl or $(C_1-C_6)$-alkoxy, $R^3$ is $(C_1-C_8)$-alkyl, $(C_2-C_8)$-alkenyl or $(C_2-C_8)$-alkynyl, each of which may be substituted by phenyl, $(C_3-C_8)$-cycloalkyl, hydroxy, $(C_1-C_6)$-alkoxy, $(C_1-C_6)$-acyloxy or amino, and $R^4$ is a group of the formula $-OR^7$ or $-NR^8R^9$, in which $R^7$ is hydrogen or $(C_1-C_6)$-alkyl, $R^8$ and $R^9$ are identical or different and are independently of one another hydrogen, $(C_1-C_6)$-alkyl or $(C_3-C_8)$-cycloalkyl, each of which may be substituted by substituents selected from the group of carboxyl, $(C_1-C_6)$-alkoxycarbonyl, aminocarbonyl, mono- and di-$(C_1-C_6)$-alkylaminocarbonyl, or $R^8$ and $R^9$ form together with the nitrogen atom to which they are bonded a 4- to 8-membered heterocycle which may comprise a further ring heteroatom from the series $N-R^{10}$, O, S, SO or $SO_2$ and may be substituted by substituents selected from the group of hydroxy, oxo, amino, $(C_1-C_6)$-alkyl, carboxyl, $(C_1-C_6)$-alkoxycarbonyl, aminocarbonyl, mono- and di-$(C_1-C_6)$alkylaminocarbonyl, in which $(C_1-C_6)$-alkyl in turn may be substituted by substituents selected from the group of hydroxy, amino, carboxyl, $(C_1-C_6)$-alkoxycarbonyl, aminocarbonyl, mono- and di-$(C_1-C_6)$alkylaminocarbonyl, and $R^{10}$ is hydrogen, $(C_1-C_4)$-alkyl, $(C_1-C_4)$-acyl or $(C_1-C_4)$-alkoxycarbonyl, and the salts, solvates and solvates of the salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methyl-morpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

In the context of the present invention, the substituents have the following meaning unless otherwise specified:

$(C_1-C_8)$-Alkyl, $(C_1-C_6)$-alkyl and $(C_1-C_4)$-alkyl are in the context of the invention a straight-chain or branched alkyl radical having respectively 1 to 8, 1 to 6 and 1 to 4 carbon atoms. A straight-chain or branched alkyl radical having 1 to 6 or 1 to 4 carbon atoms is preferred. A straight-chain or branched alkyl radical having 1 to 4 carbon atoms is particularly preferred. Examples which may be preferably mentioned are: methyl, ethyl, n-propyl, isopropyl, n-butyl, isobutyl, sec-butyl, tert-butyl, 1-ethylpropyl, n-pentyl and n-hexyl.

$(C_2-C_8)$-Alkenyl and $(C_2-C_6)$-alkenyl in the context of the invention are a straight-chain or branched alkenyl radical having respectively 2 to 8 and 2 to 6 carbon atoms. A straight-chain or branched alkenyl radical having 2 to 6 carbon atoms is preferred, particularly preferably having 2 to 4 carbon atoms. Examples which may be preferably mentioned are: vinyl, allyl, isopropenyl, n-but-2-en-1-yl and 2-methyl-2-propen-1-yl.

$(C_2-C_8)$-Alkynyl in the context of the invention is a straight-chain or branched alkynyl radical having 2 to 8 carbon atoms. A straight-chain or branched alkynyl radical having 2 to 6 carbon atoms is preferred, particularly preferably having 2 to 4 carbon atoms. Examples which may be preferably mentioned are: ethynyl, n-prop-2-yn-1-yl and n-but-2-yn-1-yl.

$(C_3-C_8)$-Cycloalkyl and $(C_3-C_6)$-cycloalkyl in the context of the invention are a monocyclic cycloalkyl group having respectively 3 to 8 and 3 to 6 carbon atoms. A cycloalkyl radical having 3 to 6 carbon atoms is preferred. Examples which may be preferably mentioned are: cyclopropyl, cyclobutyl, cyclopentyl, cyclohexyl and cycloheptyl.

$(C_6-C_{10})$-Aryl in the context of the invention is an aromatic radical having preferably 6 to 10 carbon atoms. Preferred aryl radicals are phenyl and naphthyl.

$(C_1-C_6)$-Alkoxy and $(C_1-C_4)$-alkoxy in the context of the invention are a straight-chain or branched alkoxy radical having respectively 1 to 6 and 1 to 4 carbon atoms. A straight-chain or branched alkoxy radical having 1 to 4 carbon atoms is preferred. Examples which may be preferably mentioned are: methoxy, ethoxy, n-propoxy, isopropoxy and tert-butoxy.

$(C_1-C_6)$-alkoxycarbonyl and $(C_1-C_4)$-alkoxycarbonyl in the context of the invention are a straight-chain or branched alkoxy radical having respectively 1 to 6 and 1 to 4 carbon atoms which is linked via a carbonyl group. A straight-chain or branched alkoxycarbonyl radical having 1 to 4 carbon atoms in the alkoxy group is preferred. Examples which may be preferably mentioned are: methoxycarbonyl, ethoxycarbonyl, n-propoxycarbonyl, isopropoxycarbonyl and tert-butoxy-carbonyl.

Mono- or di-$(C_1-C_6)$-alkylaminocarbonyl and mono- or di-$(C_1-C_4)$-alkylaminocarbonyl in the context of the invention are an amino group which is linked via a carbonyl group and which has respectively a straight-chain or branched and two identical or different straight-chain or branched alkyl substituents each having respectively 1 to 6 and 1 to 4 carbon atoms. Examples which may be preferably mentioned are: methylaminocarbonyl, ethylaminocarbonyl, isopropylaminocarbonyl, tert-butylaminocarbonyl, N,N-dimethylaminocarbonyl, N,N-diethylaminocarbonyl, N-ethyl-N-methylaminocarbonyl and N-tert-butyl-N-methylaminocarbonyl.

$(C_1-C_4)$-Acyl [$(C_1-C_4)$-alkanoyl] in the context of the invention is a straight-chain or branched alkyl radical having 1 to 4 carbon atoms which has a doubly bonded oxygen atom in position 1 and is linked via position 1. Examples which may be preferably mentioned are: formyl, acetyl, propionyl, n-butyryl and iso-butyryl.

$(C_1-C_6)$-Acyloxy in the context of the invention is a straight-chain or branched alkyl radical having 1 to 6 carbon atoms which has a doubly bonded oxygen atom in position 1 and is linked via a further oxygen atom in position 1. An acyloxy radical having 1 to 4 carbon atoms is preferred. Examples which may be preferably mentioned are: acetoxy, propionoxy, n-butyroxy, i-butyroxy, pivaloyloxy and n-hexanoyloxy.

5- to 10-membered heteroaryl in the context of the invention is a mono- or, where appropriate, bicyclic aromatic heterocycle (heteroaromatic system) having up to three identical or different heteroatoms from the series N, O and/or S, which is linked via a ring carbon atom or, where appropriate, via a ring nitrogen atom of the heteroaromatic system. Examples which may be mentioned are: furanyl, pyrrolyl, thienyl, pyrazolyl, imidazolyl, thiazolyl, oxazolyl, isoxazolyl, iso-thiazolyl, pyridyl, pyrimidinyl, pyridazinyl, pyrazinyl, benzofuranyl, benzothienyl, benzimidazolyl, benzoxazolyl, indolyl, indazolyl, quinolinyl, isoquinolinyl, naphthyridinyl, quinazolinyl, quinoxalinyl. 5- to 6-membered heteroaryl radicals having up to two heteroatoms from the series N, O and/or S are preferred, such as, for example, furyl, thienyl, thiazolyl, oxazolyl, isothiazolyl, isoxazolyl, imidazolyl, pyridyl, pyrimidinyl, pyridazinyl, pyrazinyl.

A 4- to 8-, 5- to 7- and 5- to 6-membered heterocycle in the context of the invention is a saturated or partially unsaturated heterocycle having respectively 4 to 8, 5 to 7 and 5 to 6 ring atoms which comprises a ring nitrogen atom, is linked via the latter and may comprise a further heteroatom from the series N, O, S, SO or $SO_2$. A 5- to 7-membered saturated, N-linked heterocycle which may comprise a further heteroatom from the series N, O or S is preferred. Examples which may be mentioned are: pyrrolidinyl, pyrrolinyl, piperidinyl, piperazinyl, morpholinyl, thiomorpholinyl, azepinyl, 1,4-diazepinyl. Piperidinyl, piperazinyl, morpholinyl and pyrrolidinyl are particularly preferred.

Halogen in the context of the invention includes fluorine, chlorine, bromine and iodine. Chlorine or fluorine are preferred.

If radicals in the compounds according to the invention are substituted, the radicals may, unless otherwise specified, be substituted one or more times. In the context of the present invention, all radicals which occur more than once have a mutually independent meaning. Substitution by one, two or three identical or different substituents is preferred. Substitution by one substituent is very particularly preferred.

Preference is given to compounds of the formula (I) in which

A is phenyl, naphthyl or pyridyl, each of which may be substituted up to twice, identically or differently, by substituents selected from the group of fluorine, chlorine, bromine, cyano, trifluoromethyl, trifluoromethoxy, $(C_1-C_4)$-alkyl, $(C_2-C_4)$-alkynyl and $(C_1-C_4)$-alkoxy, or is a group of the formula

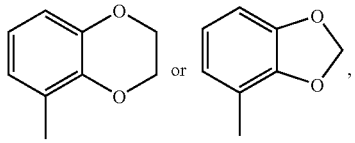

n is the number 1, 2 or 3, $R^1$ is hydrogen, fluorine, chlorine, cyano, trifluoromethyl, trifluoromethoxy, $(C_1-C_4)$-alkyl or $(C_1-C_4)$-alkoxy, $R^2$ is hydrogen, $R^3$ is $(C_1-C_6)$-alkyl or $(C_2-C_6)$-alkenyl, each of which may be substituted by phenyl, $(C_3-C_6)$-cycloalkyl or hydroxy, and $R^4$ is a group of the formula —$OR^7$ or —$NR^8R^9$ in which $R^7$ is hydrogen, $R^8$ and $R^9$ are identical or different and are independently of one another hydrogen, $(C_1-C_6)$-alkyl or $(C_3-C_6)$-cycloalkyl, each of which may be substituted by substituents selected from the group of carboxyl, $(C_1-C_4)$-alkoxycarbonyl, aminocarbonyl, mono- and di-$(C_1-C_4)$-alkylaminocarbonyl, or $R^8$ and $R^9$ form together with the nitrogen atom to which they are bonded a 5- to 7-membered heterocycle which may comprise a further ring heteroatom from the series N—$R^{10}$ and O and may be substituted by substituents selected from the group of hydroxy, oxo, amino, $(C_1$-$C_4)$-alkyl, carboxyl, $(C_1-C_4)$-alkoxycarbonyl, aminocarbonyl, mono- and di-$(C_1-C_4)$-alkylaminocarbonyl, in which $(C_1-C_4)$-alkyl in turn may be substituted by substituents selected from the group of hydroxy, amino, carboxyl, $(C_1-C_4)$-alkoxycarbonyl, aminocarbonyl, mono- and di-$(C_1-C_4)$-alkylaminocarbonyl, and $R^{10}$ is hydrogen, $(C_1-C_4)$-alkyl, $(C_1-C_4)$-acyl or $(C_1-C_4)$-alkoxycarbonyl, and the salts, solvates and solvates of the salts thereof.

Particular preference is given to compounds of the formula (I) in which

A is phenyl which may be substituted once or twice, identically or differently, by fluorine, chlorine, bromine, methyl, ethyl, ethynyl or methoxy, is naphthyl or is a group of the formula

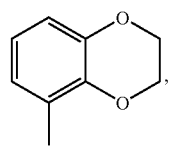

n is the number 1, $R^1$ is hydrogen, chlorine, methyl or trifluoromethyl, $R^2$ is hydrogen, $R^3$ is $(C_1-C_6)$-alkyl, $(C_2-C_6)$-alkenyl or is benzyl, and $R^4$ is a group of the formula —$OR^7$ or —$NR^8R^9$ in which $R^7$ is hydrogen, $R^8$ and $R^9$ are identical or different and are independently of one another hydrogen or $(C_1-C_6)$-alkyl which may be substituted by carboxyl or $(C_1-C_4)$alkoxycarbonyl, or $R^8$ and $R^9$ form together with the nitrogen atom to which they are bonded a 5- to 6-membered heterocycle which may comprise a further ring heteroatom from the series N—$R^{10}$ and O and may be substituted by substituents selected from the group of hydroxy, oxo, amino, $(C_1$-$C_4)$-alkyl, carboxyl, $(C_1-C_4)$-alkoxycarbonyl, aminocarbonyl, mono- and di-$(C_1-C_4)$-alkylaminocarbonyl, in which $(C_1-C_4)$-alkyl in turn may be substituted by substituents selected from the group of hydroxy, amino, carboxyl, $(C_1-C_4)$-alkoxycarbonyl, aminocarbonyl, mono- and di-$(C_1-C_4)$-alkylaminocarbonyl, and $R^{10}$ is hydrogen, $(C_1-C_4)$-alkyl or $(C_1-C_4)$-acyl, and the salts, solvates and solvates of the salts thereof.

Very particular preference is given to compounds of the formula (I-A)

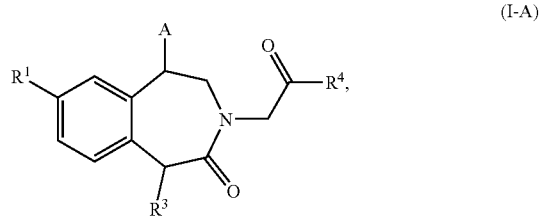

in which

A is phenyl which is substituted once or twice, identically or differently, by fluorine, chlorine, bromine, methyl, ethynyl or methoxy, or is a group of the formula

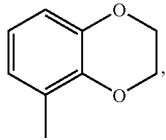

$R^1$ is chlorine, methyl or trifluoromethyl, $R^3$ is $(C_1-C_6)$-alkyl or $(C_2-C_6)$-alkenyl, and $R^4$ is a group of the formula —$OR^7$ or —$NR^8R^9$ in which $R^7$ is hydrogen, $R^8$ and $R^9$ are identical or different and are independently of one another hydrogen or $(C_1-C_6)$-alkyl which may be substituted by carboxyl or $(C_1-C_4)$-alkoxycarbonyl, or $R^8$ and $R^9$ form together with the nitrogen atom to which they are bonded a 5- to 6-membered heterocycle which may comprise a further ring heteroatom from the series N—$R^{10}$ and O and may be substituted by substituents selected from the group of hydroxy, oxo, amino, $(C_1-C_4)$-alkyl, carboxyl, $(C_1-C_4)$-alkoxycarbonyl, aminocarbonyl, mono- and di-$C_1$-$C_4$)-alkylaminocarbonyl, in which $(C_1-C_4)$-alkyl in turn may be substituted by substituents selected from the group of hydroxy, amino, carboxyl, $(C_1-C_4)$-alkoxycarbonyl, aminocarbonyl, mono- and di-$(C_1-C_4)$-alkylaminocarbonyl, and $R^{10}$ is hydrogen, $(C_1-C_4)$-alkyl or $(C_1-C_4)$-acyl, and the salts, solvates and solvates of the salts thereof.

The definitions of radicals indicated specifically in the respective combinations or preferred combinations of radicals are replaced as desired irrespective of the particular combinations indicated for the radicals also by the definitions of radicals of other combinations.

Combinations of two or more of the abovementioned preferred ranges are very particularly preferred.

The invention further relates to a process for preparing the compounds according to the invention, characterized in that compounds of the formula (II)

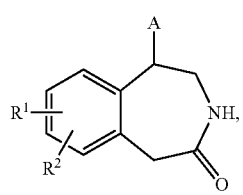

in which $R^1$, $R^2$ and A each have the abovementioned meanings, are firstly reacted in an inert solvent in the presence of a base with a compound of the formula (III)

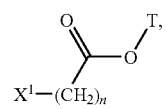

in which n has the abovementioned meanings,

T is $(C_1-C_4)$-alkyl or benzyl and $X^1$ is a suitable leaving group such as, for example, halogen, mesylate or tosylate, to give compounds of the formula (IV)

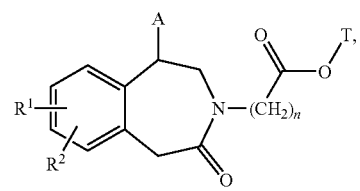

in which $R^1$, $R^2$, A, T and n each have the abovementioned meanings, subsequently converted in an inert solvent in the presence of a suitable base, preferably a phosphazene base, with a compound of the formula (V)

$$R^3—X^2 \qquad (V),$$

in which $R^3$ has the abovementioned meanings, and $X^2$ is a suitable leaving group such as, for example, halogen, mesylate or tosylate, into compounds of the formula (VI)

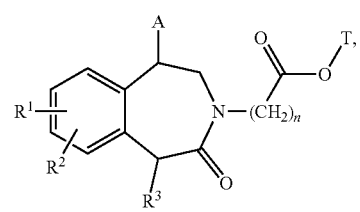

in which $R^1$, $R^2$, $R^3$, A, T and n each have the abovementioned meanings, the latter are converted by basic or acidic hydrolysis, or in the case where T is benzyl also by hydrogenolysis, into carboxylic acids of the formula (VII)

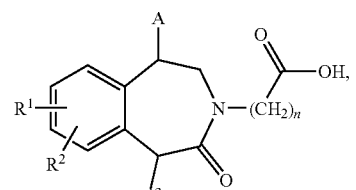

in which $R^1$, $R^2$, $R^3$, A and n each have the abovementioned meanings, and then converted by methods known from the literature for the esterification or amidation of carboxylic acids into the compounds of the formula (I), and the compounds of the formula (I) are reacted where appropriate with the appropriate (i) solvents and/or (ii) bases or acids to give the solvates, salts and/or solvates of the salts thereof.

Examples of inert solvents for process step (II)+(III)→(IV) are halohydrocarbons such as dichloromethane, trichloromethane, tetrachloromethane, trichloroethane, tetrachloroethane, 1,2-dichloroethane or trichloroethylene, ethers such as diethyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as ethyl acetate, acetone, dimethylformamide, dimethyl sulphoxide, N,N'-dimethylpropyleneurea (DMPU), N-methyl-pyrrolidone (NMP), pyridine or acetonitrile. It is likewise possible to employ mixtures of the said solvents. Dimethylformamide is preferred.

Bases suitable for process step (II)+(III)→(IV) are the usual inorganic or organic bases. These preferably include alkali metal hydroxides such as, for example, lithium, sodium or potassium hydroxide, alkali metal or alkaline earth metal carbonates such as lithium, sodium, potassium, calcium or caesium carbonate, alkali metal alcoholates such as sodium or potassium methanolate, sodium or potassium ethanolate or potassium tert-butoxide, alkali metal hydrides such as sodium hydride, amides such as sodamide, lithium or potassium bis(trimethylsilyl)amide or lithium diisopropylamide, or organic bicyclic amines such as 1,5-diazabicyclo[4.3.0]non-5-ene (DBN), 1,4-diazabicyclo[2.2.2]octane (DABCO®) or 1,8-diazabicyclo[5.4.0]undec-7-ene (DBU). Caesium carbonate is preferred.

The compound of the formula (III) and the base are in this case each employed in an amount of from 1 to 5 mol, preferably in an amount of from 1.5 to 2.5 mol, based on 1 mol of the compound of the formula (II). The reaction generally takes place in a temperature range from −20° C. to +100° C., preferably from 0° C. to +40° C. The reaction can be carried out under atmospheric, elevated or reduced pressure (e.g. from 0.5 to 5 bar). It is generally carried out under atmospheric pressure.

Examples of inert solvents for process step (IV)+(V)→(VI) are ethers such as diethyl ether, dioxane, tetrahydrofuran, glycol dimethyl ether or diethylene glycol dimethyl ether, hydrocarbons such as benzene, xylene, toluene, hexane, cyclohexane or petroleum fractions, or dimethylformamide. It is likewise possible to employ mixtures of the said solvents. Tetrahydrofuran or tetrahydrofuran/hexane mixtures are preferred.

Bases suitable and preferred for process step (IV)+(V)→(VI) are phosphazene bases (so-called "Schwesinger bases") such as, for example, 1-tert-butyl-2,2,4,4,4-pentakis(dimethylamino)-$2\lambda^5,4\lambda^5$-catenadi(phosphazene) or 3-tert-butyl-imino-1,1,1,5,5,5-hexakis(dimethylamino)-3-[tris(dimethylamino)phosphoranylidene]amino-$1\lambda^5,3\lambda^5,5\lambda^5$-1,4-triphosphazadiene [cf., for example, R. Schwesinger, H. Schlemper, *Angew. Chem. Int. Ed. Engl.* 26, 1167 (1987); T. Pietzonka, D. Seebach, *Chem. Ber.* 124, 1837 (1991)]. The base is in this case employed in an amount of from 1 to 3 mol, preferably in an amount of from 1.1 to 2 mol, based on 1 mol of the compound of the formula (IV).

The compound of the formula (V) is employed in this process step in an amount of from 1 to 5 mol, preferably in an amount of from 2 to 4 mol, based on 1 mol of the compound of the formula (IV). The reaction generally takes place in a temperature range from −100° C. to 0° C., preferably from −80° C. to −20° C. The reaction can be carried out under atmospheric, elevated or reduced pressure (e.g. from 0.5 to 5 bar). It is generally carried out under atmospheric pressure.

Examples of inert solvents for process step (VI)→(VII) are halohydrocarbons such as dichloromethane, 1,2-dichloroethane or trichloroethylene, ethers such as diethyl ether, dioxane, tetrahydrofuran, glycol dimethyl ether or diethylene glycol dimethyl ether, alcohols such as methanol, ethanol, n-propanol, isopropanol, n-butanol or tert-butanol, hydrocarbons such as benzene, xylene, toluene, hexane, cyclohexane or petroleum fractions, or other solvents such as acetone, dimethylformamide, dimethyl sulphoxide, acetonitrile, N-methylpyrrolidinone or else water. It is likewise possible to use mixtures of the said solvents. Dioxane/water, tetrahydrofuran/water, methanol/water or tetrahydrofuran/methanol/water mixtures are preferably employed.

Bases for process step (VI)→(VII) are the usual inorganic bases. These preferably include alkali metal hydroxides such as, for example, lithium, sodium or potassium hydroxide, or alkali metal or alkaline earth metal carbonates such as sodium, potassium or calcium carbonate. Sodium hydroxide is particularly preferred. The base is employed in this case in an amount of from 1 to 5, preferably from 1.5 to 3, mol based on 1 mol of the compound of the formula (VI).

Acids suitable for process step (VI)→(VII) are aqueous solutions of the usual inorganic acids such as, for example, hydrochloric acid, sulphuric acid, phosphoric acid or hydrobromic acid, or sulphonic acids such as toluenesulphonic acid, methanesulphonic acid or trifluoromethanesulphonic acid, or carboxylic acids such as trifluoroacetic acid.

The reaction generally takes place in a temperature range from −20° C. to +100° C., preferably from 0° C. to +40° C. The reaction can be carried out under atmospheric, elevated or reduced pressure (e.g. from 0.5 to 5 bar). It is generally carried out under atmospheric pressure.

Process step (VII)→(I) is carried out by methods known from the literature for the esterification or amidation (amide formation) of carboxylic acids.

Examples of inert solvents for an amidation in process step (VII)→(I) are ethers such as diethyl ether, dioxane, tetrahydrofuran, glycol dimethyl ether or diethylene glycol dimethyl ether, hydrocarbons such as benzene, toluene, xylene, hexane, cyclohexane or petroleum fractions, halohydrocarbons such as dichloromethane, trichloromethane, tetrachloromethane, 1,2-dichloroethane, trichloroethylene or chlorobenzene, or other solvents such as ethyl acetate, pyridine, dimethyl sulphoxide, dimethylformamide, N,N'-dimethylpropyleneurea (DMPU), N-methylpyrrolidone (NMP), acetonitrile or acetone. It is likewise possible to employ mixtures of the said solvents. Dichloromethane, tetrahydrofuran, dimethylformamide or mixtures of these solvents are preferred.

Condensing agents suitable for an amidation in process step (VII)→(I) are, for example, carbodiimides such as N,N'-diethyl-, N,N'-dipropyl-, N,N'-diisopropyl-, N,N'-dicyclohexylcarbodiimide (DCC), N-3-dimethylaminoisopropyl)-N'-ethylcarbodiimide hydrochloride (EDC), or phosgene derivatives such as N,N'-carbonyldiimidazole, or 1,2-oxazolium compounds such as 2-ethyl-5-phenyl-1,2-oxazolium-3-sulphate or 2-tert-butyl-5-methylisoxazolium perchlorate, or acylamino compounds such as 2-ethoxy-1-ethoxycarbonyl-1,2-dihydroquinoline, or isobutyl chloroformate, propanephosphonic anhydride, diethyl cyanophosphonate, bis(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzo-triazol-1-yl)-N,N,N',N'-tetramethyluronium hexafluorophosphate (HATU), where appropriate in combination with further auxiliaries such as 1-hydroxybenzotriazole (HOBt) or N-hydroxysuccinimide (HOSu), and suitable bases are alkali metal carbonates, e.g. sodium or potassium carbonate or bicarbonate, or organic bases such as trialkylamines, e.g. triethylamine, N-methylmorpholine, N-methylpiperidine or N,N-diisopropylethylamine. EDC in combination with HOBt and N,N-diisopropylethylamine, HATU in combination with N,N-diisopropylethylamine or else diethyl cyanophosphonate in combination with triethylamine is preferably used.

An amide formation in process step (VII)→(I) is generally carried out in a temperature range from 0° C. to +100° C., preferably from 0° C. to +40° C. The reaction can be carried out under atmospheric, elevated or reduced pressure (e.g. from 0.5 to 5 bar). It is generally carried out under atmospheric pressure.

The compounds of the formula (II) can be prepared in analogy to processes known from the literature, for example by Schmidt reaction with trimethylsilyl azide/sulphuric acid [cf., for example, F. Pozgan, S. Polanc, M. Kocevar, *Heterocycles* 56, 379 (2002)] from tetralone derivatives of the formula (VIII)

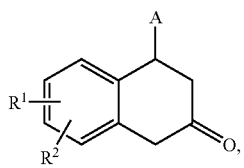

(VIII)

in which $R^1$, $R^2$ and A each have the abovementioned meanings.

The compounds of the formula (VIII) are known from the literature or can be prepared in analogy to processes known from the literature [cf., for example, a): I. Fleming, A. Pearce, *J. Chem. Soc. Perkin I* 1980, 2485; R. S. Prasad, R. M. Roberts, *Synth Commun.* 21, 3385 (1991); b): G. Bertolini, V. Vecchietti, M. Mabilia, G. Norcini, A. Restelli, F. Santangelo, A. M. Villa, C. Casagrande, *Eur. J. Med. Chem.* 27, 663-672 (1992); c): S. D. Wyrick, R. G. Booth, A. M. Myers, C. E. Owens, N. S. Kula, R. J. Baldessarini, A. T. McPhail, R. B. Mailman, *J. Med. Chem.* 36, 2542 (1993); E. C. Bucholtz, R. L. Brown, A. Tropsha, R. G. Booth, S. D. Wyrick, *J. Med. Chem.* 42, 3041 (1999)].

The compounds of the formula (II) can also be prepared by first converting isochromanone derivatives of the formula (IX)

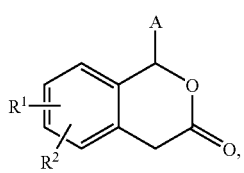

(IX)

in which $R^1$, $R^2$ and A each have the abovementioned meanings, with trimethylsilyl cyanide with catalysis by iodine and/or trimethylsilyl iodide into compounds of the formula (X)

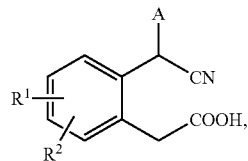

(X)

in which $R^1$, $R^2$ and A each have the abovementioned meanings, esterifying the latter with trimethylsilyl chloride in methanol, preferably in a one-pot reaction, to give compounds of the formula (XI)

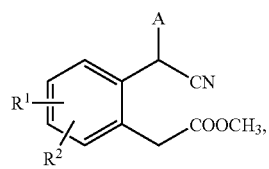

(XI)

in which $R^1$, $R^2$ and A each have the abovementioned meanings, subsequently converting by hydrogenation in the presence of a Raney nickel catalyst or by reduction with sodium borohydride in the presence of nickel chloride or cobalt(II) chloride to give compounds of the formula (XII)

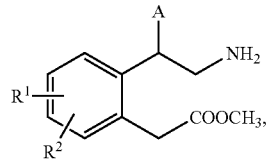

(XII)

in which $R^1$, $R^2$ and A each have the abovementioned meanings, and cyclizing the latter by heating in an inert solvent such as, for example, toluene, preferably in a one-pot reaction, to give the compounds of the formula (II) [cf. also Busacca et al., *Tetrahedron Lett.* 33 (2), 169 (1998)].

The compounds of the formula (IX) are known or can be prepared in analogy to processes known from the literature [cf., for example, G. Brancaccio et al., *J. Med Chem.* 24, 998-1000 (1981); M. Shindo et al., *J. Org. Chem.* 66, 7818-7824 (2001); see also scheme 2].

The compounds of the formulae (III) and (V) are commercially available, known from the literature or can be prepared in analogy to processes known from the literature.

The preparation of the compounds according to the invention can be illustrated by the following synthesis schemes:

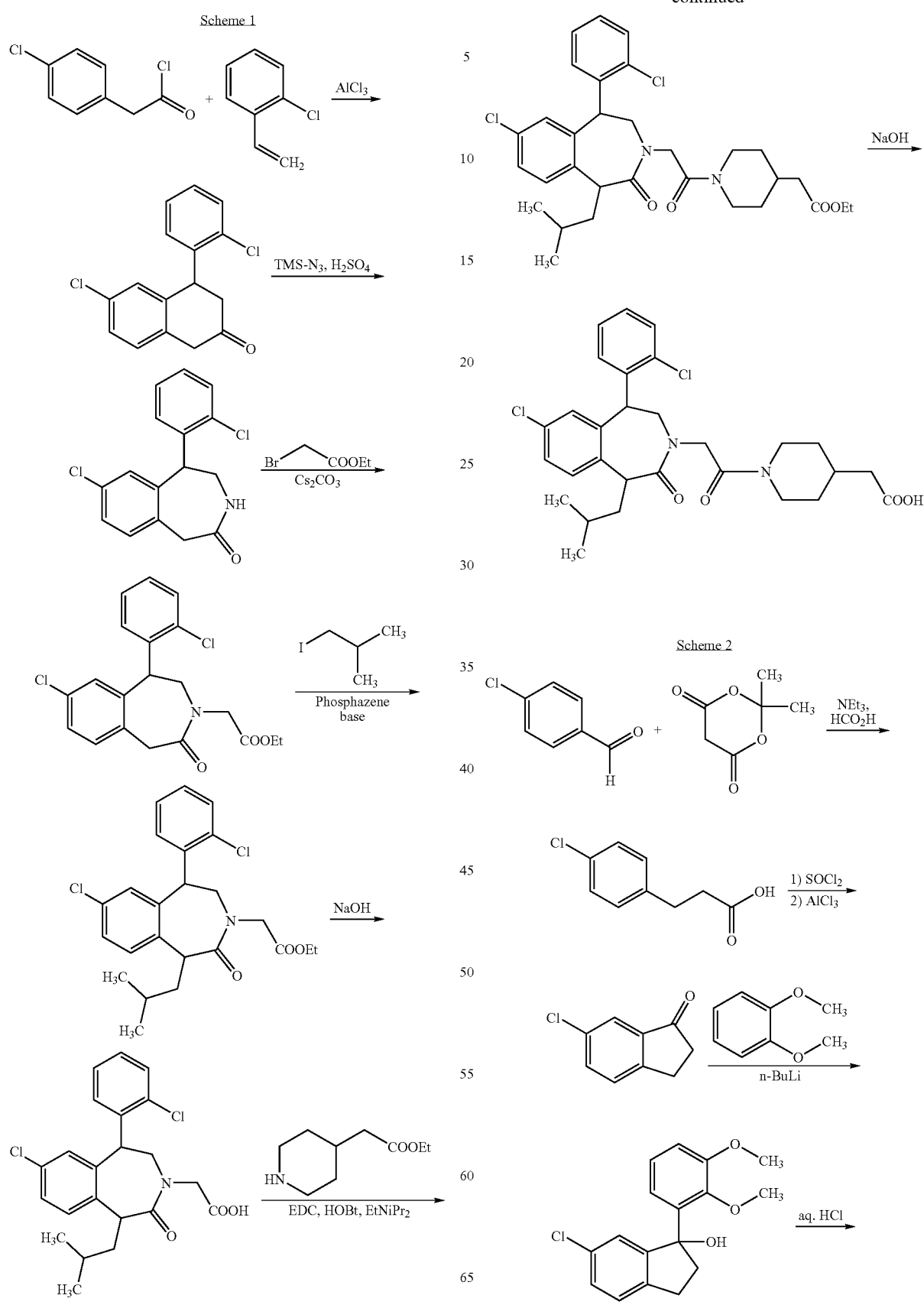

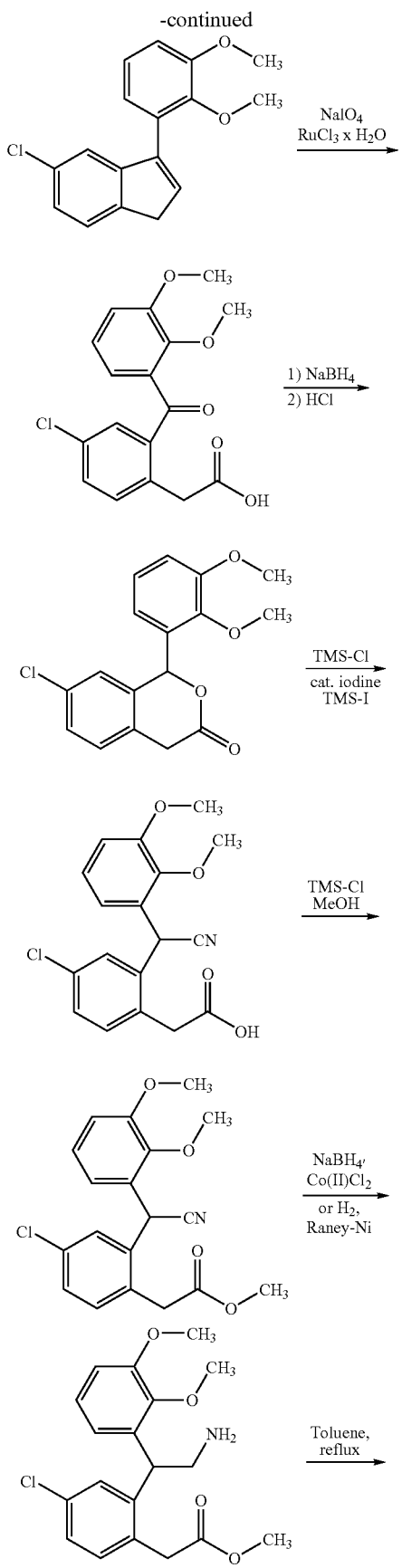

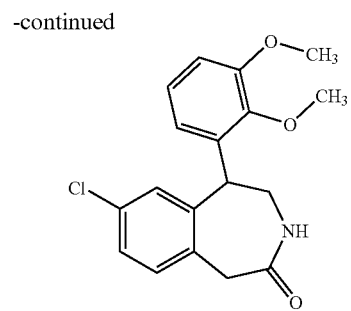

[Abbreviations: aq.=aqueous; Bu=butyl; cat.=catalytic; EDC=N'-(3-dimethylaminopropyl)-N-ethylcarbodiimide hydrochloride; Et=ethyl; HOBt=1-hydroxy-1H-benzotriazole hydrate; Me=methyl; $^{i}$Pr=isopropyl; TMS=trimethylsilyl].

The compounds according to the invention have valuable pharmacological properties and can be used for the prevention and treatment of disorders in humans and animals. In particular, the compounds according to the invention are highly effective inhibitors of squalene synthase and inhibit cholesterol biosynthesis. The compounds according to the invention bring about a lowering of the cholesterol level and of the triglyceride level in the blood. They can therefore be employed for the treatment and prevention of cardiovascular disorders, in particular of hypolipoproteinaemia, dyslipidaemias, hyperlipidaemias or arteriosclerosis. The compounds according to the invention may additionally be used for the treatment and prevention of adiposity and corpulence (obesity). The compounds according to the invention are further suitable for the treatment and prevention of strokes and of Alzheimer's disease.

The present invention further relates to the use of the compounds according to the invention for the treatment and/or prophylaxis of disorders, in particular of the aforementioned disorders.

The present invention further relates to the use of the compounds according to the invention for producing a medicament for the treatment and/or prophylaxis of disorders, especially of the aforementioned disorders.

The present invention further relates to a method for the treatment and/or prophylaxis of disorders, in particular of the aforementioned disorders, using an effective amount of at least one of the compounds according to the invention.

The present invention further relates to medicaments comprising at least one compound according to the invention and at least one or more further active ingredients, in particular for the treatment and/or prophylaxis of the aforementioned disorders. Examples which may be preferably mentioned of active ingredients suitable for combination are: cholesterol-lowering statins, cholesterol absorption inhibitors, HDL-elevating or triglyceride-lowering and/or apolipoprotein B-lowering substances, oxidation inhibitors or compounds having antiinflammatory activity. Combinations with these active ingredients are preferably suitable for the treatment of dyslipidaemias, combined hyperlipidaemias, hypercholesterolaemias or hypertriglyceridaemias.

The said combinations can also be employed for the primary or secondary prevention of coronary heart disease (e.g. myocardial infarction) and for peripheral arterial disorders.

Examples of statins in the context of the invention are lovastatin, simvastatin, pravastatin, fluvastatin, atorvastatin, rosuvastatin and pitavastatin. Examples of cholesterol absorption inhibitors are cholestyramines or ezetimibe; examples of HDL-elevating or triglyceride-lowering or apolipoprotein B-lowering substances are fibrates, niacin, PPAR agonists, IBAT inhibitors, MTP inhibitors and CETP inhibitors. Compounds having antiinflammatory activity are, for example, aspirin.

The present invention further relates additionally to the combination of the compounds according to the invention with a glucosidase inhibitor and/or amylase inhibitor for the treatment of familial hyperlipidaemia, of adiposity (obesity) and of diabetes mellitus.

Examples of glucosidase inhibitors and/or amylase inhibitors in the context of the invention are acarbose, adiposins, voglibose, miglitol, emiglitates, MDL-25637, camiglibose (MDL-73945), tendamistats, AI-3688, trestatin, pradimicin Q and salbostatin. Combination of acarbose, miglitol, emiglitates or voglibose with one of the compounds according to the invention is preferred.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colours (e.g. inorganic pigments such as, for example, iron oxides) and masking flavours and/or odours.

The present invention further relates to medicaments which comprise at least one compound according to the invention, normally together with one or more inert, non-toxic, pharmaceutically suitable excipients, and to the use thereof for the aforementioned purposes.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations:
CI chemical ionization (in MS)
DMF N,N-dimethylformamide
DMSO dimethyl sulphoxide
ESI electrospray ionization (in MS)
GC/MS coupled gas chromatography-mass spectroscopy
h hour(s)
HPLC high pressure, high performance liquid chromatography
LC/MS coupled liquid chromatography-mass spectroscopy
min. minute(s)
MS mass spectroscopy
NMR nuclear magnetic resonance spectroscopy
RT room temperature
$R_t$ retention time (in HPLC)
THF tetrahydrofuran LC/MS, GC/MS and HPLC Methods:
Method 1:
MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 2:
Instrument: Micromass Quattro LCZ with HPLC Agilent Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 3:

MS instrument type: Micromass ZQ; HPLC instrument type: HP 1100 Series; UV DAD; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 4:

Instrument: Micromass GCT, GC 6890; column: Restek RTX-35MS, 30 m×250 µm×0.25 µm; constant flow with helium: 0.88 ml/min; oven: 60° C.; inlet: 250° C.; gradient: 60° C. (hold for 0.30 min), 50° C./min→120° C., 16° C./min→250° C., 30° C./min→300° C. (hold for 1.7 min).

Method 5:

Instrument: HP 1100 with DAD detection; column: Kromasil RP-18, 60 mm×2 mm, 3.5 µm; eluent A: 5 ml of $HClO_4$/l of water, eluent B: acetonitrile; gradient: 0 min 2% B→0.5 min 2% B→4.5 min 90% B→6.5 min 90% B; flow rate: 0.75 ml/min; oven: 30° C.; UV detection: 210 nm.

Method 6:

Instrument: HP 1100 with DAD detection; column: Kromasil RP-18, 60 mm×2 mm, 3.5 µm; eluent A: 5 ml of $HClO_4$/l of water, eluent B: acetonitrile; gradient: 0 min 2% B→0.5 min 2% B→4.5 min 90% B→9 min 90% B; flow rate: 0.75 ml/min; oven: 30° C.; UV detection: 210 nm.

Starting Compounds and Intermediates:

Example 1A

6-Chloral-4-(2-chloroprene)-3,4-dihedron-1H-naphthalene-2-one

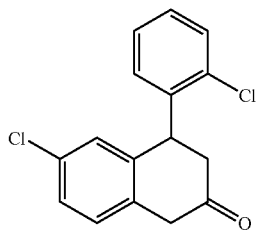

Under an argon atmosphere, 1.59 g of aluminum dichloride (7.93 mol) are suspended in 80 ml of dichloromethane and, at 0° C., a solution of 1.50 g of 4-chlorophenylacetyl chloride (11.90 mol) in 40 ml of dichlormethane is added. At 0° C., a solution of 1.65 g of 2-chlorostyrene (11.90 mol) in 100 ml of dichloromethane is added drop wise over the course of 30 min. The reaction mixture is poured into 300 ml of ice-water and extracted three times with dichloromethane. The combined organic phases are dried over sodium sulphate and concentrated in a rotary evaporator. The residue is purified by chromatography on silica gel (mobile phase: cyclohexane/ethyl acetate 7:1). 0.795 g (31% of theory) of the title compound is obtained.

$^1$H-NMR (400 MHz, $CDCl_3$): δ=2.84-2.94 (m, 2H), 3.65 (d, J=20.4, 1H), 3.73 (d, J=20.4, 1H), 4.93 (t, J=6.8, 1H), 6.88-6.91 (m, 2H), 7.15-7.17 (m, 1H), 7.20-7.27 (m, 3H), 7.45-7.47 (m, 1H). LC/MS (method 1): $R_t$=2.64 min.; MS (ESIpos): m/z=291 [M+H]$^+$.

Example 2A

7-Chloral-5-(2-chloroprene-1,3,4,5-tetrahydrobenzo[d]azepin-2-one

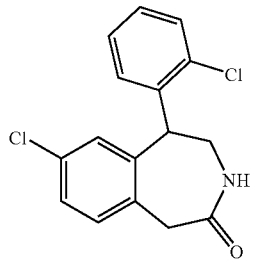

2.16 g of the compound from Example 1A (7.40 mol) are dissolved in 90 ml of dichloromethane, and 7.4 ml of concentrated sulphuric acid are added. While cooling in ice, a solution of 1.28 g of trimethylsilyl azide (11.11 mol) in 15 ml of dichloromethane is added drop wise. The reaction mixture is stirred at room temperature for 1 h and then poured into 300 ml of ice-water. The aqueous phase is made weakly basic (pH 8) by adding sodium bicarbonate in portions. The organic phase is separated off, and the aqueous phase is extracted three times with dichloromethane. The combined organic phases are washed twice with saturated sodium bicarbonate solution, dried over sodium sulphate and concentrated in a rotary evaporator. The residue is purified by chromatography on silica gel (mobile phase: cyclohexane/ethyl acetate 2:3→1:2). 0.65 g (29% of theory) of the title compound is obtained.

$^1$H-NMR (400 MHz, $CDCl_3$): δ=3.63-3.71 (m, 1H), 3.83-3.90 (m, 1H), 3.94 (s, 1H), 4.91 (dd, J=6.9 und 4.0, 1H), 5.74-5.81 (m, 1H), 6.74-6.76 (m, 1H), 6.87 (s, 1H), 7.13-7.22 (m, 4H), 7.41-7.43 (m, 1H). LC/MS (method 2): $R_t$=2.44 min.; MS (ESIpos): m/z=306 [M+H]$^+$.

Example 3A

Ethyl[8-chloro-1-(2-chloroprene)-4-oxo-1,2,4,5-tetrahydrobenzo[d]azepin-3-yl]acetate

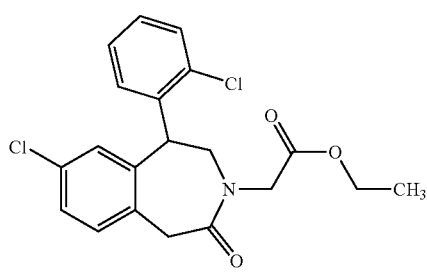

300 mg of the compound from Example 2A (0.98 mol) are dissolved in 6 ml of dimethylformamide, and 638 mg of caesium carbonate (1.96 mol) are added. 220 µl of ethyl bromoacetate (327 mg, 1.96 mol) are added drop wise, and the suspension is stirred at room temperature overnight. 9 ml of water are added, and the mixture is extracted three times with dichloromethane. The combined organic phases are dried over sodium sulphate and concentrated in a rotary evaporator. The residue is purified by preparative HPLC (eluent: acetonitrile/water with 0.1% formic acid, gradient 20:80→95:5). 132 mg (34% of theory) of the title compound are obtained.

$^1$H-NMR (400 MHz, CDCl$_3$): δ=1.22 (t, J=7.2, 3H), 3.33-3.39 (m, 1H), 3.92-3.97 (m, 3H), 4.11-4.28 (m, 4H), 5.03 (t, J=5.8, 1H), 6.72-6.74 (m, 1H), 6.88 (s, 1H), 7.15-7.22 (m, 4H), 7.41-7.43 (m, 1H). LC/MS (method 3): R$_t$=2.70 min.; MS (ESIpos): m/z=392 [M+H]$^+$.

Example 4A

Ethyl 4-piperidylacetate

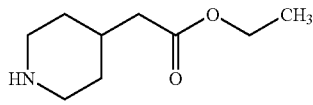

2.0 g of ethyl 4-pyridylacetate in 20 ml of ethanol are mixed with 400 mg of palladium black (20% by weight), adjusted to pH 2 with 1 N hydrochloric acid and hydrogenated under 3 bar at room temperature for 2 days. Solids are filtered off with suction through kieselguhr, and the solvent is removed from the filtrate under reduced pressure. The residue is taken up in 50 ml of ethyl acetate and 50 ml of water. The aqueous phase is adjusted to pH 13 with 1 N sodium hydroxide solution and extracted twice with 50 ml of ethyl acetate each time. The combined organic phases are dried over magnesium sulphate, and the solvent is removed under reduced pressure. 1.21 g (58% of theory) of the product are obtained.

GC/MS (method 4): R$_t$=5.93 min., m/z=172 [M+H]$^+$.

Example 5A

Ethyl[7-chloro-5-(2-chloroprene)-1-(2-methylallyl)-2-oxo-1,2,4,5-tetrahydrobenzo[d]azepin-3-yl]acetate

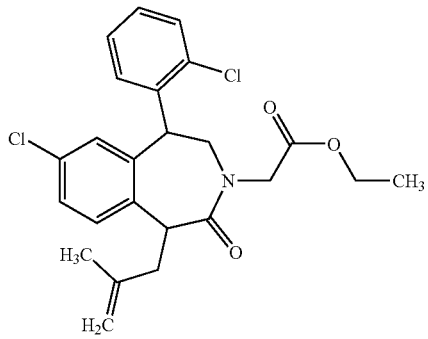

39 mg of the compound from Example 3A (0.10 mol) and 30 µl of 3-broom-2-methylpropene (41 mg, 0.30 mol) are dissolved in 550 µl of THF. At −78° C., 75 µl (0.15 mol) of a 2 M solution of 1-tert-butyl-2,2,4,4,4-pentakis(dimethylamino)-2λ$^5$-4λ$^5$-catenadi(phosphazene) in THF are added drop wise, and the reaction mixture is stirred at −78° C. for 4.5 h. The reaction solution is mixed with 1 ml of 1 M hydrochloric acid and water and extracted three times with dichloromethane. The combined organic phases are washed twice with saturated sodium bicarbonate solution, dried over sodium sulphate and concentrated in a rotary evaporator. The residue is purified by preparative HPLC (eluent: acetonitrile/water with 0.1% formic acid, gradient 20:80→95:5). 27 mg (60% of theory) of the title compound are obtained.

$^1$H-NMR (400 MHz, CDCl$_3$): δ=1.20 (t, J=7.2, 3H), 1.87 (s, 3H), 2.71 (dd, J=15.7 and 6.1, 1H), 2.97 (dd, J=15.7 and 8.0, 1H), 3.78 (dd, J=15.7 and 5.6, 1H), 3.88-4.01 (m, 1H), 4.10-4.27 (m, 4H), 4.67-4.69 (m, 1H), 4.72 (s, 1H), 4.87 (s, 1H), 5.11 (dd, J=10.9 and 6.5, 1H), 6.85-6.88 (m, 1H), 6.91-6.94 (m, 1H), 7.14-7.24 (m, 4H), 7.40-7.44 (m, 1H). LC/MS (method 2): R$_t$=3.12 min.; MS (ESIpos): m/z=445 [M+H]$^+$.

Example 6A

Ethyl[7-chloro-5-(2-chloroprene)-1-isobutyl-2-oxo-1,2,4,5-tetrahydrobenzo[d]azepin-3-yl]-acetate

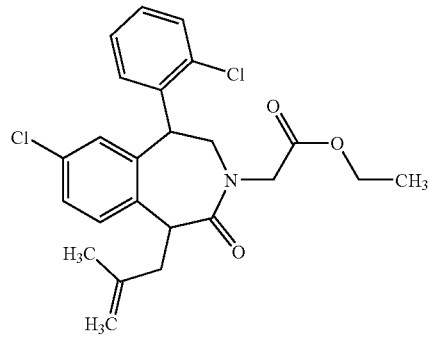

505 mg of the compound from Example 3A (1.29 mol) are dissolved in 5 ml of THF. At −78° C., 1.93 ml of a 1 M solution of 3-tert-butylimino-1,1,1,5,5,5-hexakis(dimethylamino)-3-[tris(dimethylamino)phosphoranylidene]amino-1λ$^5$,3λ$^5$,5λ$^5$-1,4-triphosphazadiene in THF are added drop wise, and the reaction solution is stirred at −78° C. for 30 min. 0.45 ml of 1-iodo-2-methylpropane (711 mg, 3.86 mol) is added drop wise, and the mixture is stirred at −78° C. for a further 2 h. The reaction solution is mixed with 5 ml of 1 N hydrochloric acid and water and extracted three times with dichloromethane. The combined organic phases are washed twice with saturated sodium bicarbonate solution, dried over sodium sulphate and concentrated in a rotary evaporator. The residue is purified by preparative HPLC (eluent: acetonitrile/water with 0.1% formic acid, gradient 20:80→95:5). 149 mg (26% of theory) of the title compound are obtained.

$^1$H-NMR (400 MHz, CDCl$_3$): δ=1.01 (d, J=7.3, 3H); 1.02 (d, J=6.9, 3H), 1.20 (t, J=7.1, 3H), 1.67-1.84 (m, 2H), 2.21-2.28 (m, 1H), 3.55-4.28 (m, 6H), 4.39-4.50 (m, 1H), 5.04-5.08 (m, 1H), 6.79-6.81 (m, 1H), 6.92 (s, 1H), 7.14-7.27 (m, 4H), 7.41-7.43 (m, 1H). LC/MS (method 1): R$_t$=3.07 min.; MS (ESIpos): m/z 448 [M+H]$^+$.

Example 7A 4-(2-Chloroprene)-6-methyl-3,4-dihedron-1H-naphthalene-2-one

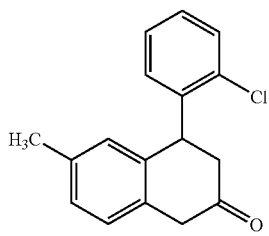

Under an argon atmosphere, 5.93 g of aluminum dichloride (44.48 mol) are suspended in 250 ml of dichloromethane and, at −20° C., a solution of 5.00 g of p-tolylacetyl chloride (29.65 mol) in 150 ml of dichloromethane is added. At −20° C., a solution of 6.16 g of 2-chlorostyrene (44.48 mol) in 350 ml of dichloromethane is added drop wise over the course of 30 min. The reaction mixture is poured into 1000 ml of ice-water and extracted three times with dichloromethane. The combined organic phases are dried over sodium sulphate and concentrated in a rotary evaporator. The residue is purified by chromatography on silica gel (mobile phase: cyclohexane/ethyl acetate 15:1). 4.80 g (60% of theory) of the title compound are obtained.

$^1$H-NMR (400 MHz, CDCl$_3$): δ=2.26 (s, 3H), 2.83-2.96 (m, 2H), 3.62 (d, J=20.4, 1H), 3.72 (d, J=20.4, 1H), 4.93 (t, J=6.5, 1H), 6.57 (s, 1H), 6.84-6.87 (m, 1H), 7.06-7.23 (m, 4H), 7.42-7.45 (m, 1H). HPLC (method 5): R$_t$=5.15 min.; MS (CI): m/z=288 [M+NH$_4$]$^+$.

Example 8A 4-(2-Bromophenyl)-6-chloro-3,4-dihedron-1H-naphthalene-2-one

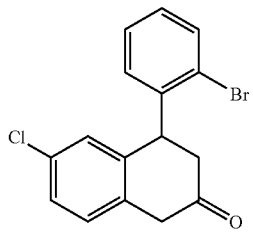

Under an argon atmosphere at 0° C., 5.01 g of aluminum dichloride (38.24 mol) are suspended in 400 ml of dichloromethane and, at the same temperature, a solution of 4.82 g of 4-chloroprene-acetyl chloride (25.49 mol) in 200 ml of dichloromethane is added. At 0° C., a solution of 7.00 g of 2-bromostyrene (38.24 mol) in 500 ml of dichloromethane is added drop wise over the course of 30 min. After stirring at 0° C. for 10 min, the reaction mixture is poured into 1000 ml of ice-water and extracted three times with dichloromethane. The combined organic phases are dried over sodium sulphate and concentrated in a rotary evaporator. The residue is purified by chromatography on silica gel (mobile phase: cyclohexane/ethyl acetate 25:1→15:1). 4.46 g (51% of theory) of the title compound are obtained.

$^1$H-NMR (400 MHz, CDCl$_3$): δ=2.88 (d, J=7.0, 2H), 3.65 (d, J=20.4, 1H), 3.74 (d, J=20.4, 1H), 4.93 (t, J=7.0, 1H), 6.88-6.91 (m, 2H), 7.15-7.29 (m, 2H), 7.42-7.29 (m, 2H), 7.65 (dd, J=7.9, J=1.2, 1H). HPLC (method 5): R$_t$=5.22 min.; MS (CI): m/z=352 [M+NH$_4$]$^+$.

Example 9A 5-(2-Chloroprene)-7-methyl-1,3,4,5-tetrahydrobenzo[d]azepin-2-one

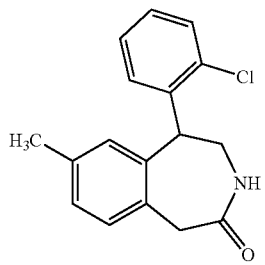

4.80 g of the compound from Example 7A (17.73 mol) are dissolved in 250 ml of dichloromethane, and 20.0 ml of concentrated sulphuric acid are added. While cooling in ice, a solution of 3.06 g of trimethylsilyl azide (3.53 ml, 26.59 mol) in 55 ml of dichloromethane is added drop wise. The reaction mixture is stirred at room temperature for 1 h and then poured into 1500 ml of ice-water. The aqueous phase is made weakly basic (pH 8) by adding sodium bicarbonate in portions. The organic phase is separated off, and the aqueous phase is extracted three times with dichloromethane. The combined organic phases are washed twice with saturated sodium bicarbonate solution, dried over sodium sulphate and concentrated in a rotary evaporator. The residue is purified by chromatography on silica gel (mobile phase: cyclohexane/ethyl acetate 2:3→1:2). 1.48 g (29% of theory) of the title compound are obtained.

$^1$H-NMR (400 MHz, CDCl$_3$): δ=2.18 (s, 3H), 3.58-3.68 (m, 1H), 3.85-3.88 (m, 1H), 3.88 (d, J=14.5, 1H), 3.97 (d, J=14.5, 1H), 4.90-4.94 (m, 1H), 5.54-5.64 (m, 1H), 6.67 (s, 1H), 6.74-6.76 (m, 1H), 6.97-7.00 (m, 1H), 7.07-7.20 (m, 3H), 7.39-7.42 (m, 1H). HPLC (method 5): R$_t$=4.51 min.; MS (CI): m/z=286 [M+H]$^+$.

Example 10A 5-(2-Bromophenyl)-7-chloro-1,3,4,5-tetrahydrobenzo[d]azepin-2-one

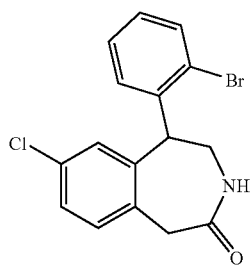

5.80 g of the compound from Example 8A (17.28 mol) are dissolved in 250 ml of dichloromethane, and 20.0 ml of concentrated sulphuric acid are added. While cooling in ice, a solution of 2.99 g of trimethylsilyl azide (3.44 ml, 25.92 mol)

in 55 ml of dichloromethane is added drop wise. The reaction mixture is stirred at room temperature for 1 h and then poured into 1500 ml of ice-water. The aqueous phase is made weakly basic (pH 8) by adding sodium bicarbonate in portions. The organic phase is separated off and the aqueous phase is extracted three times with dichloromethane. The combined organic phases are washed twice with saturated sodium bicarbonate solution, dried over sodium sulphate and concentrated in a rotary evaporator. The residue is purified by chromatography on silica gel (mobile phase: cyclohexane/ethyl acetate 1:1→1:3). 1.59 g (24% of theory) of the title compound are obtained.

$^1$H-NMR (400 MHz, CDCl$_3$): δ=3.62-3.69 (m, 1H), 3.84-3.91 (m, 1H), 3.94 (s, 2H), 4.91 (dd, J=6.7, J=3.9, 1H), 5.63-5.67 (m, 1H), 6.72-6.75 (m, 1H), 6.86 (s, 1H), 7.10-7.22 (m, 4H), 7.61 (dd, J=7.9, J=1.3, 1H). HPLC (method 6): R$_t$=4.63 min.; MS (CI): m/z=367 [M+NH$_4$]$^+$.

Example 11A

Ethyl[1-(2-chloroprene)-8-methyl-4-oxo-1,2,4,5-tetrahydrobenzo[d]azepin-3-yl]acetate

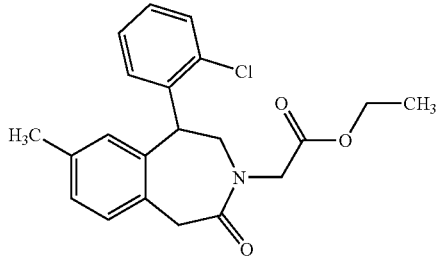

1400 mg of the compound from Example 9A (4.90 mol) are dissolved in 30 ml of dimethylformamide, and 3192 mg of caesium carbonate (9.80 mol) are added. 1.09 ml of ethyl bromoacetate (1636 mg, 9.80 mol) are added drop wise, and the suspension is stirred at room temperature overnight. Water is added, and the mixture is extracted three times with dichloromethane. The combined organic phases are dried over sodium sulphate and concentrated in a rotary evaporator. The residue is purified by preparative HPLC (eluent: acetonitrile/water with 0.1% formic acid, gradient 20:80→95:5). 670 mg (37% of theory) of the title compound are obtained.

$^1$H-NMR (400 MHz, CDCl$_3$): δ=1.22 (t, J=7.2, 3H), 2.18 (s, 3H), 3.27 (d, J=17.5, 1H), 3.85-4.18 (m, 6H), 4.22 (d, J=17.5, 1H), 4.99-5.02 (m, 1H), 6.68-6.72 (m, 2H), 6.97-6.99 (m, 1H), 7.08-7.21 (m, 3H), 7.40-7.42 (m, 1H). LC/MS (method 2): R$_t$=2.67 min.; MS (ESIpos): m/z=372 [M+H]$^+$.

Example 12A

Ethyl[1-(2-bromophenyl)-8-chloro-4-oxo-1,2,4,5-tetrahydrobenzo[d]azepin-3-yl]acetate

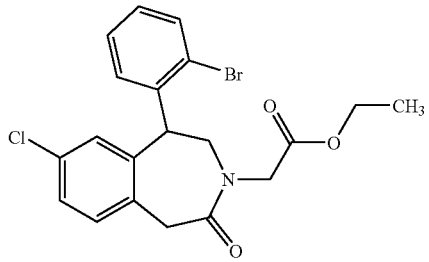

1500 mg of the compound from Example 10A (4.28 mol) are dissolved in 30 ml of dimethylformamide, and 2788 mg of caesium carbonate (8.56 mol) are added. 0.95 ml of ethyl bromoacetate (1429 mg, 8.56 mol) is added drop wise, and the suspension is stirred at room temperature overnight. Water is added, and the mixture is extracted three times with dichloromethane. The combined organic phases are dried over sodium sulphate and concentrated in a rotary evaporator. The residue is purified by preparative HPLC (eluent: acetonitrile/water with 0.1% formic acid, gradient 20:80→95:5). 450 mg (24% of theory) of the title compound are obtained.

HPLC (method 6): R$_t$=5.08 min.; MS (CI): m/z=453 [M+NH$_4$]$^+$.

Example 13A

Ethyl[5-(2-chloroprene)-1-isobutyl-7-methyl-2-oxo-1,2,4,5-tetrahydrobenzo[d]azepin-3-yl]acetate

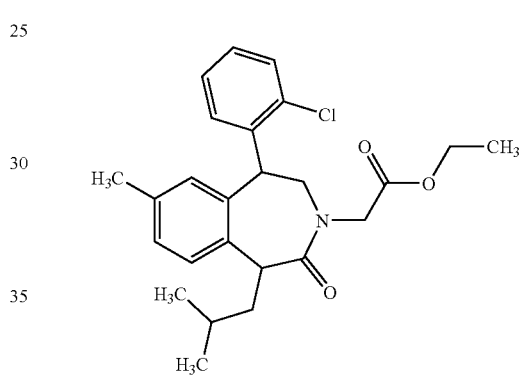

660 mg of the compound from Example 11A (1.77 mol) are dissolved in 9.2 ml of THF. At −78° C., 2.66 ml of a 1 M solution of 3-tert-butylimino-1,1,1,5,5,5-hexakis(dimethylamino)-3-[tris(dimethylamino)phosphoranylidene]amino-1λ$^5$,3λ$^5$,5λ$^5$-1,4-triphosphazadiene in n-hexane are added drop wise, and the reaction solution is stirred at −78° C. for 45 min. 490 mg of 1-iodo-2-methylpropane (2.66 mol) are added drop wise, and the mixture is stirred at −78° C. for a further 3 h. The reaction solution is mixed with 25 ml of 1 N hydrochloric acid and water and extracted three times with dichloromethane. The combined organic phases are washed twice with saturated sodium bicarbonate solution, dried over sodium sulphate and concentrated in a rotary evaporator. The residue is purified by preparative HPLC (eluent: acetonitrile/water with 0.1% formic acid, gradient 20:80→95:5). 410 mg (54% of theory) of the title compound are obtained.

$^1$H-NMR (400 MHz, CDCl$_3$): δ=1.01 (d, J=6.2, 3H), 1.02 (d, J=6.4, 3H), 1.20 (t, J=7.2, 3H), 1.68-1.88 (m, 2H), 2.15-2.28 (m, 1H), 2.18 (s, 3H), 3.95-4.22 (m, 3H), 4.13 (q, J=7.2, 2H), 4.38-4.43 (m, 1H), 5.04 (t, J=7.4, 1H), 6.72 (s, 1H), 6.78-6.81 (m, 1H), 6.99-7.03 (m, 1H), 7.10-7.20 (m, 3H), 7.39-7.42 (m, 1H). LC/MS (method 2): R$_t$=3.21 min.; MS (ESIpos): m/z=428 [M+H]$^+$.

Example 14A

Ethyl[5-(2-bromophenyl)-7-chloro-1-isobutyl-2-oxo-1,2,4,5-tetrahydrobenzo[d]azepin-3-yl]-acetate

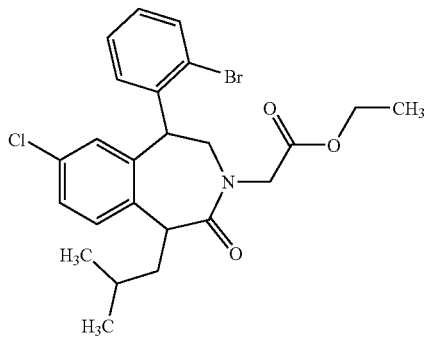

440 mg of the compound from Example 12A (1.01 mol) are dissolved in 5.2 ml of THF. At −78° C., 1.51 ml of a 1 M solution of 3-tert-butylimino-1,1,1,5,5,5-hexakis(dimethylamino)-3-[tris(dimethylamino)phosphoranylidene]amino-1λ$^5$,3λ$^5$,5λ$^5$-1,4-triphosphazadiene in n-hexane (1.51 mol) are added drop wise, and the reaction mixture is stirred at −78° C. for 30 min. 278 mg of 1-iodo-2-methylpropane (1.51 mol) are added drop wise, and the mixture is stirred at −78° C. for a further 3 h. The reaction solution is mixed with 14 ml of 1 N hydrochloric acid and water and extracted three times with dichloromethane. The combined organic phases are washed twice with saturated sodium bicarbonate solution, dried over sodium sulphate and concentrated in a rotary evaporator. The residue is purified by preparative HPLC (eluent: acetonitrile/water with 0.1% formic acid, gradient 20:80→95:5). 200 mg (40% of theory) of the title compound are obtained.

$^1$H-NMR (400 MHz, CDCl$_3$): δ=1.01 (d, J=6.2, 3H), 1.02 (d, J=6.4, 3H), 1.20 (t, J=7.2, 3H), 1.66-1.87 (m, 2H), 2.20-2.30 (m, 1H), 3.83-4.19 (m, 2H), 4.14 (q, J=7.2, 2H), 4.23 (d, J=17.4, 1H), 4.41-4.48 (m, 1H), 5.05 (t, J=7.6, 1H), 6.78-6.81 (m, 1H), 6.92 (s, 1H), 7.09-7.24 (m, 4H), 7.61 (dd, J=7.8, J=1.4, 1H). LC/MS (method 3): R$_t$=3.24 min.; MS (ESIpos): m/z=492 [M+H]$^+$.

Example 15A 3-(4-Chloroprene)propionic acid

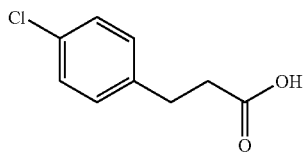

48.2 g of triethylamine (67.2 ml, 0.48 mol) are added drop wise to 55.2 g of formic acid (45.3 ml, 1.20 mol) while stirring and cooling. At room temperature, 28.1 g of 4-chlorobenzaldehyde (0.20 mol), 28.8 g of Meldrum's acid (0.20 mol) and 100 ml of DMF are added to this mixture. The mixture is slowly heated while stirring to 95° C. and is stirred at this temperature for a further 2 h. After cooling, the reaction mixture is acidified to pH 1 with 6 N hydrochloric acid and stored at 5° C. for 16 h. The crystallized target compound is filtered off and dried under high vacuum. 32.4 g (88% of theory) of the title compound are obtained.

$^1$H-NMR (400 MHz, DMSO-4): δ=2.53 (t, J=7.6, 3H), 2.80 (d, J=7.6, 3H), 7.24-7.27 (m, 2H), 7.32-7.34 (m, 2H), 12.14 (br. s, 1H). LC/MS (method 1): R$_t$=1.75 min.; MS (ESIneg): m/z=183 [M−H]$^-$.

Example 16A

6-Chloroindan-1-one

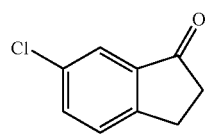

55.0 g of the compound from Example 15A (297.8 mol) are suspended in 212.7 g of thionyl chloride (130 ml, 1788.5 mol), and the mixture is heated under reflux for 1 h. The excess thionyl chloride is distilled out, the residue is taken up in dichloromethane, and the solvent is removed in a rotary evaporator. The resulting crude acid chloride is reacted further without further purification. For this purpose, 60.5 g of the acid chloride (297.9 mol) are dissolved in 100 ml of n-heptane, and a total of 47.7 g of aluminum dichloride (357.5 mol) is added in portions. The addition takes place in such a way that the temperature of the mixture does not exceed 25° C. The reaction mixture is stirred at room temperature for 4 h and then slowly poured into 500 ml of ice-water. The mixture is extracted four times with ethyl acetate, and the combined organic phases are dried over sodium sulphate. The solution is concentrated to a remaining volume of 200 ml and is stored at 5° C. for 16 h. The crystallized target compound is filtered off, washed with a little n-pentane and dried under high vacuum. 34.1 g (69% of theory) of the title compound result.

$^1$H-NMR (400 MHz, CDCl$_3$): δ=2.71-2.75 (m, 2H), 3.10-3.14 (m, 1H), 7.40-7.43 (m, 1H), 7.53-7.56 (m, 1H), 7.71-7.72 (m, 1H). LC/MS (method 2): R$_t$=2.09 min.; MS (ESIpos): m/z=167 [M+H]$^+$.

Example 17A 2-(5-Chloro-1H-inden-3-yl)phenyl methyl ether

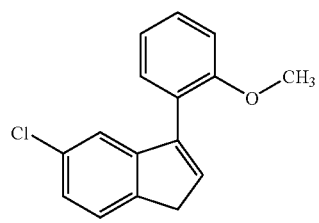

Under an argon atmosphere, a solution of 12.80 g of 6-chloroindan-1-one (73.45 mol) from Example 16A in 60 ml of THF is added drop wise to 88 ml of a 1 M solution of 2-methoxyphenylmagnesium bromide in THF (88.0 mol) at 0° C. The reaction mixture is stirred at room temperature 1.5 h and 200 ml of 1 N hydrochloric acid are added for working up. The mixture is extracted three times with ethyl acetate, the combined organic phases are dried over sodium sulphate, and the solvent is removed in a rotary evaporator. The residue is dissolved in 400 ml of dichloromethane, mixed with 0.10 g of 4-toluenesulphonic acid monohydrate (0.53 mol) and stirred at room temperature for 16 h. The reaction mixture is washed with saturated sodium bicarbonate solution and saturated sodium chloride solution and dried over sodium sulphate. The solvent is removed in a rotary evaporator, and the residue is purified by chromatography on silica gel (mobile phase: cyclohexane/ethyl acetate 150:1). 12.02 g (61% of theory) of the title compound are obtained.

$^1$H-NMR (400 MHz, CDCl$_3$): δ=3.50 (d, J=2.0, 2H), 3.81 (s, 3H), 6.62 (t, J=2.0, 1H), 6.99-7.06 (m, 2H), 7.15-7.22 (m, 2H), 7.33-7.42 (m, 3H). LC/MS (method 3): R$_t$=3.10 min.; MS (ESIpos): m/z=257 [M+H]$^+$.

Example 18A

[4-Chloro-2-(2-methoxybenzoyl)phenyl]acetic acid

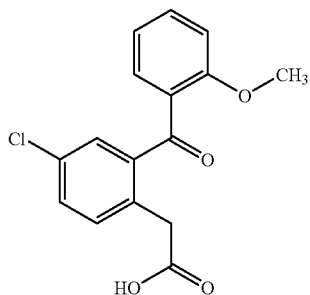

12.02 g of the compound from Example 17A (44.76 mol) are mixed with 120 ml of acetonitrile, 120 ml of hexane and 180 ml of water. 39.25 g of sodium periodate (183.51 mol) and 0.18 g of ruthenium(III) chloride hydrate (0.81 mol) are added, and the mixture is stirred at room temperature for 48 h. For working up, the reaction mixture is acidified with a 5% aqueous trifluoroacetic acid solution and extracted three times with methylene chloride. The combined organic phases are washed with saturated sodium chloride solution and dried over sodium sulphate, and the solvent is removed in a rotary evaporator. The residue is taken up in ethyl acetate, and the solution is stored at 5° C. for 16 h. The deposited crystals are filtered off and dried under high vacuum. 5.12 g (38% of theory) of the title compound are obtained.

$^1$H-NMR (400 MHz, CDCl$_3$): δ=3.68 (s, 3H), 3.85 (s, 2H), 6.96 (d, J=8.3, 1H), 7.07 (t, J=7.5, 1H), 7.35-7.48 (m, 3H), 7.53-7.59 (m, 2H). LC/MS (method 1): R$_t$=1.97 min.; MS (ESIpos): m/z=305 [M+H]$^+$.

Example 19A

7-Chloro-1-(2-methoxyphenyl)-1,4-dihedron-3H-isochroman-3-one

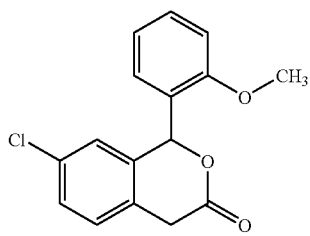

898 mg of the compound from Example 18A (2.95 mol) are dissolved in 25 ml of ethanol. 167 mg of sodium borohydride (4.42 mol) are added, and the reaction mixture is stirred at room temperature for 16 h. The reaction solution is mixed with 20 ml of 20% strength hydrochloric acid and diluted with water, the organic phase is removed in a rotary evaporator, and the remaining aqueous phase is extracted three times with dichloromethane. The combined organic phases are dried over sodium sulphate, and the solvent is removed in a rotary evaporator. The residue is purified by chromatography in silica gel (mobile phase: cyclohexane/ethyl acetate 5:1). 712 mg (83% of theory) of the title compound are obtained.

$^1$H-NMR (400 MHz, CDCl$_3$): δ=3.80 (s, 2H), 3.85 (s, 3H), 6.73 (s, 1H), 6.80 (s, 1H), 6.98-7.05 (m, 2H), 7.17-7.32 (m, 2H), 7.38-7.43 (m, 1H). LC/MS (method 1): R$_t$=2.35 min.; MS (ESIpos): m/z=389 [M+H]$^+$.

Example 20A

Methyl{4-chloro-2-[cyano(2-methoxyphenyl)methyl]phenyl}acetate

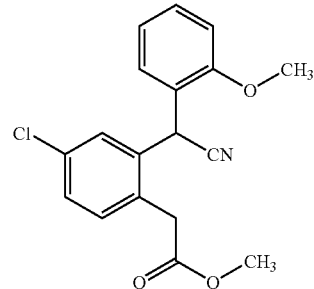

2.462 g of the compound from Example 19A (8.53 mol) are dissolved in 85 ml in ethanol, and 1.015 g of trimethylsilyl cyanide (10.23 mol) and 0.108 g of iodine (0.43 mol) are added. The reaction mixture is stirred at room temperature for 16 h and then a further 0.443 mg of trimethyl-silyl cyanide (4.26 mol) and 0.108 g of iodine (0.43 mol) are added. After stirring at room temperature for 16 h, 10 ml of water and 30 ml of acetonitrile are added, and the mixture is stirred at 40° C. for 20 min and then concentrated in a rotary evaporator. The residue is dissolved in 60 ml of methanol and, after drop wise addition of 1.947 g of trimethylsilyl chloride (17.92 mol), stirred at room temperature for 16 h. The solvent is removed in a rotary evaporator, and the residue is purified by chromatography on silica gel (mobile phase: cyclohexane/ethyl acetate 5:1). 1.20 g (43% of theory) of the title compound are obtained.

$^1$H-NMR (400 MHz, CDCl$_3$): δ=3.54 (d, J=16.0, 1H), 3.62 (s, 3H), 3.65 (d, J=16.0, 1H), 3.85 (s, 3H), 5.69 (s, 1H), 6.89-6.91 (m, 1H), 6.96-6.99 (m, 1H), 7.18-7.35 (m, 4H), 7.49-7.50 (m, 1H). LC/MS (method 3): R$_t$=2.66 min.; MS (ESIpos): m/z=330 [M+H]$^+$.

Example 21A

7-Chloro-5-(2-methoxyphenyl)-1,3,4,5-tetrahydro-2H-3-benzazepin-2-one

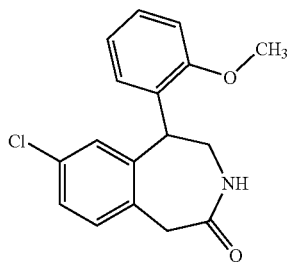

201 mg of the compound from Example 20A (0.61 mol) are dissolved in 30 ml of ethanol, introduced into a hydrogenation apparatus and mixed with anhydrous Raney nickel. The catalyst has previously been obtained by washing 1.0 ml of a 50% strength aqueous Raney nickel suspension with ethanol several times. Hydrogenation is carried out under atmospheric pressure and at room temperature for 2.5 h. The catalyst is then filtered off under an argon atmosphere and washed three times with ethanol, and the combined filtrates are concentrated. The residue is dissolved in 30 ml of toluene and heated under reflux for 5 h. The solvent is removed in a rotary evaporator, and the residue is purified by preparative HPLC (eluent: acetonitrile/water, gradient 20:80→95:5). 55 mg (30% of theory) of the title compound are obtained.

$^1$H-NMR (400 MHz, CDCl$_3$): δ=3.72 (t, J=6.3, 2H), 3.82 (d, J=14.6, 1H), 3.83 (s, 3H), 4.02 (d, J=14.6, 1H), 4.76 (t, J=6.3, 1H), 5.77-5.81 (m, 1H), 6.73 (dd, J=7.4, J=1.1, 1H), 6.84-6.91 (m, 3H), 7.10-7.11 (m, 2H), 7.21-7.25 (m, 1H). LC/MS (method 2): R$_t$=2.29 min.; MS (ESIpos): m/z=302 [M+H]$^+$.

Example 22A

Ethyl[8-chloro-1-(2-methoxyphenyl)-4-oxo-1,2,4,5-tetrahydro-3H-3-benzazepin-3-yl]acetate

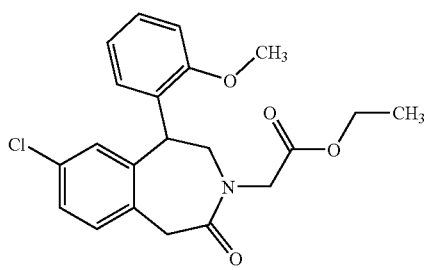

254 mg of the compound from Example 21A (0.84 mol) are dissolved in 5 ml of DMF, and 549 mg of caesium carbonate (1.68 mol) and 190 µl of ethyl bromoacetate (281 mg, 1.68 mol) are added. The reaction mixture is stirred at room temperature overnight. 6 ml of water are added, and the mixture is extracted three times with dichloromethane. The combined organic phases are washed with saturated sodium chloride solution and dried over sodium sulphate. The solvent is removed in a rotary evaporator, and the residue is purified by preparative HPLC (eluent: acetonitrile/water, gradient 20:80→95:5). 254 mg (29% of theory) of the title compound are obtained.

$^1$H-NMR (400 MHz, CDCl$_3$): δ=1.22 (t, J=7.2, 3H), 3.40-3.46 (m, 1H), 3.79-4.05 (m, 3H), 3.83 (s, 3H), 4.83-4.86 (m, 1H), 6.71-6.73 (m, 1H), 6.84-6.91 (m, 3H), 7.11 (s, 2H), 7.22-7.24 (m, 1H). LC/MS (method 2): R$_t$=2.59 min.; MS (ESIpos): m/z=388 [M+H]$^+$.

Example 23A

Ethyl[7-chloro-1-isobutyl-5-(2-methoxyphenyl)-2-oxo-1,2,4,5-tetrahydro-3H-3-benzazepin-3-yl]-acetate

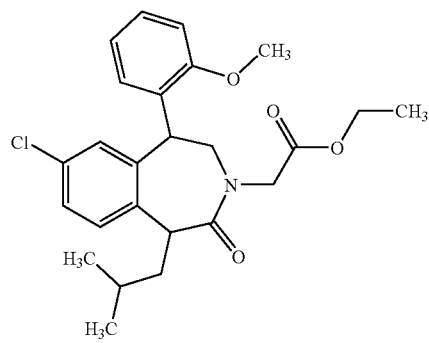

134 mg of the compound from Example 22A (0.35 mol) are dissolved in 1.35 ml of THF. At −78° C., 0.52 ml of a 1 M solution of 3-tert-butylimino-1,1,1,5,5,5-hexakis(dimethylamino)-3-(tris(dimethylamino)phosphoranylidene)amino-1λ$^5$,3λ$^5$,5λ$^5$-1,4-triphosphazadiene (P$_4$-t-Bu; 328 mg, 0.52 mol) in n-hexane is added drop wise, and the reaction solution is stirred at −78° C. for 30 min. 191 mg of 1-iodo-2-methylpropane (1.04 mol) are added drop wise, and the mixture is stirred at −78° C. for a further 2 h. The reaction solution is mixed with 10 ml of 1 N hydrochloric acid and water and extracted three times with dichloromethane. The combined organic phases are washed with saturated sodium bicarbonate solution, dried over sodium sulphate and concentrated in a rotary evaporator. The residue is purified by preparative HPLC (eluent: acetonitrile/water, gradient 20:80→95:5). 87 mg (57% of theory) of the title compound are obtained.

$^1$H-NMR (400 MHz, CDCl$_3$): δ=1.00 (d, J=6.8, 3H), 1.03 (d, J=7.2, 3H), 1.19 (t, J=7.2, 3H), 1.61-1.85 (m, 2H), 2.23-2.32 (m, 1H), 3.68-4.28 (m, 4H), 3.81 (s, 3H), 4.12 (q, J=7.2, 2H), 4.52-4.59 (m, 1H), 4.82 (dd, J=10.2, J=6.4, 1H), 6.82-6.95 (m, 4H), 7.10-7.27 (m, 3H). LC/MS (method 2): R$_t$=3.10 min.; MS (ESIpos): m/z=444 [M+H]$^+$.

Example 24A

5-Chloro-3-(2,3-dimethoxyphenyl)-1H-indene

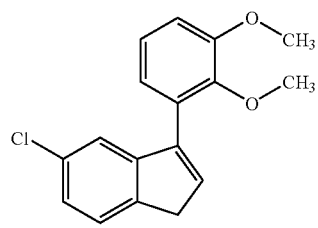

Under an argon atmosphere, 45.9 ml of veratrole (49.78 g, 360.1 mol) are dissolved in 240 ml of THF and, at −78° C., 236.2 ml of a 1.6 M solution of n-butyllithium in THF (377.7 mol) are added drop wise. The reaction mixture is warmed to 0° C. and stirred at this temperature for 3 h. The mixture is cooled to −60° C., and 30.0 g of the compound from Example 16A (180.1 mol) dissolved in 150 ml of THF are added drop wise. The reaction mixture is warmed to room temperature over the course of 3 h and then acidified with 1 N hydrochloric acid and extracted with dichloromethane. The combined organic phases are dried over magnesium sulphate, and the solvent is removed in a rotary evaporator. The residue is is purified by filtration through silica gel (mobile phase: cyclohexane/ethyl acetate 5:1). The crude product [6-chloro-1-(2, 3-dimethoxyphenyl)indan-1-ol] is dissolved in 1 l of dichloromethane and, after addition of 75 mg of 4-toluenesulphonic acid monohydrate (0.39 mol), stirred at RT for. 16 h. The reaction solution is washed with saturated sodium bicarbonate solution and with saturated sodium chloride solution, dried over sodium sulphate and concentrated in a rotary evaporator. The residue is purified by chromatography on silica gel (mobile phase: cyclohexane/ethyl acetate 20:1). 10.5 g (20% of theory) of the title compound are obtained.

$^{1}$H-NMR (400 MHz, CDCl$_{3}$): δ=3.51 (d, J=1.8, 2H), 3.63 (s, 3H), 3.93 (s, 3H), 6.66 (t, J=1.8, 1H), 6.95-6.97 (m, 2H), 7.12 (dd, J=8.3, J=7.5, 1H), 7.19 (dd, J=7.9, J=2.0, 1H), 7.34 (d, J=1.8, 1H), 7.41 (d, J=7.9, 1H). LC/MS (method 2): R$_{t}$=3.00 min.; MS (ESIpos): m/z=287 [M+H]$^{+}$.

Example 25A

[4-Chloro-2-(2,3-dimethoxybenzyl)phenyl]acetic acid

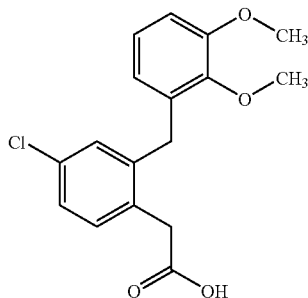

701.6 mg of sodium periodate (3.28 mol) and 3.6 mg of ruthenium(III) chloride monohydrate (0.02 mol) are introduced into 3 ml of water. 229.4 mg of the compound from Example 24A (0.80 mol) dissolved in 2 ml of tetrachloromethane are added and, after addition of 2 ml of acetonitrile, the reaction mixture is stirred at room temperature for 16 h. For working up, the mixture is poured into 20 ml of a 5% strength aqueous trifluoroacetic acid solution and extracted three times with dichloromethane. The combined organic phases are dried over sodium sulphate, and the solvent is removed in a rotary evaporator. The residue is stirred with 5 ml of ethyl acetate and 2 ml of n-heptane and stored at 5° C. for 3 h. The deposited product is filtered off, washed with m-pentane and dried under high vacuum. 119.0 mg (44% of theory) of the title compound are obtained.

$^{1}$H-NMR (400 MHz, CDCl$_{3}$): δ=3.61 (s, 3H), 3.90 (s, 5H), 7.05 (dd, J=6.4, J=2.8, 1H), 7.11-7.15 (m, 2H), 7.35-7.39 (m, 2H), 7.46 (dd, J=8.3, J=2.1, 1H). LC/MS (method 2): R$_{t}$=2.19 min.; MS (ESIpos): m/z=335 [M+H]$^{+}$.

Example 26A

7-Chloro-1-(2,3-dimethoxyphenyl)-1,4-dihedron-3H-isochroman-3-one

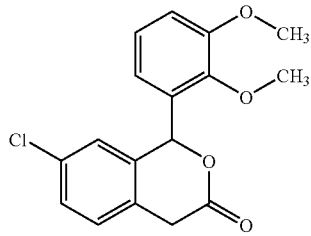

1.607 g of the compound from Example 25A (4.80 mol) are dissolved in 48 ml of ethanol. 0.182 g of sodium borohydride (4.80 mol) are added, and the reaction mixture is heated under reflux for 1 h. After cooling, 120 ml of 10% strength hydrochloric acid are added, and the mixture is concentrated in a rotary evaporator until only an aqueous phase remains. The product separates out during this. The precipitation is completed by cooling the mixture to room temperature. The precipitate is filtered off and dried under high vacuum. 1.319 g (86% of theory) of the title compound are obtained.

$^{1}$H-NMR (400 MHz, CDCl$_{3}$): δ=3.81 (s, 2H), 3.87 (s, 3H), 3.93 (s, 3H), 6.71 (s, 1H), 6.78-6.81 (m, 2H), 7.00 (dd, J=8.3, J=1.5, 1H), 7.11 (t, J=7.9, 1H), 7.19 (d, J=8.1, 1H), 7.31 (dd, J=8.0, J=2.0, 1H). LC/MS (method 1): R$_{t}$=2.28 min.; MS (ESIpos): m/z=319 [M+H]$^{+}$.

Example 27A

Methyl{4-chloro-2-[cyano(2,3-dimethoxyphenyl) methyl]phenyl}acetate

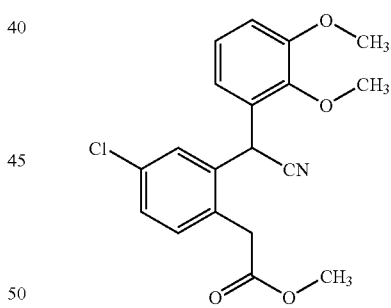

Under an argon atmosphere, 1.478 g of the compound from Example 26A (4.64 mol) are dissolved in 35 ml of dichloromethane and, at 0° C., 552 mg of trimethylsilyl cyanide (5.56 mol) and 59 mg of iodine (0.23 mol) are added. At 0° C., 46 mg of iodotrimethylsilane (0.23 mol) are added drop wise, and the reaction mixture is stirred at room temperature for 16 h. A further 139 mg of iodotrimethylsilane (0.69 mol) are added, and the mixture is stirred at room temperature for a further 6 h. The reaction mixture is mixed with 20 ml of methanol, stirred at room temperature for 15 min and then concentrated in a rotary evaporator. The residue is dissolved in 30 ml of methanol, mixed with 151 mg of chlorotrimethylsilane (1.39 mol) and stirred at room temperature for 16 h. The reaction mixture is concentrated in a rotary evaporator, and the residue is purified by chromatography on silica gel (mobile phase: cyclohexane/ethyl acetate 3:1). 902 mg (54% of theory) of the title compound are obtained.

¹H-NMR (400 MHz, CDCl₃): δ=3.56 (d, J=15.8), 3.65 (s, 3H), 3.68 (d, J=15.8, 1H), 3.73 (s, 3H), 3.87 (s, 3H), 5.76 (s, 1H), 6.87-6.89 (m, 1H), 6.92-6.94 (m, 1H), 7.07 (t, J=8.1, 1H), 7.20 (d, J=8.3, 1H), 7.28 (dd, J=8.2, J=2.1, 1H), 7.47 (d, J=2.2, 1H). LC/MS (method 2): $R_t$=2.65 min.; MS (ESIpos): m/z=360 [M+H]⁺.

Example 28A

7-Chloro-5-(2,3-dimethoxyphenyl)-1,3,4,5-tetrahydro-2H-3-benzazepin-2-one

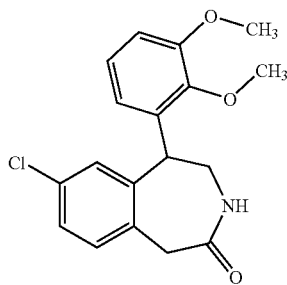

118 mg of the compound from Example 27A (0.33 mol) are dissolved in 2.3 ml of methanol, and 156 mg of cobalt(II) chloride hexahydrate (0.66 mol) are added. While stirring at 0° C., 133 mg of sodium borohydride (3.51 mol) are added in portions over the course of 10 min. The reaction mixture is stirred at 0° C. for 30 min and at room temperature for 1 h. For working up, 7 ml of 1 N hydrochloric acid are added, and the mixture is stirred until a homogeneous solution results. The solution is made basic with concentrated ammonia solution and extracted with dichloromethane. The combined organic phases are dried over sodium sulphate and concentrated in a rotary evaporator. The residue is dissolved in 10 ml of toluene and heated under reflux for 16 h. The solvent is removed in a rotary evaporator, and the residue is purified by preparative HPLC (eluent: acetonitrile/water, gradient 20:80→95:5). 42 mg (40% of theory) of the title compound are obtained.

¹H-NMR (400 MHz, CDCl₃): δ=3.53-3.62 (m, 1H), 3.56 (s, 3H), 3.68 (d, J=14.5, 1H), 3.85-3.94 (m, 1H), 3.88 (s, 3H), 4.20 (d, J=14.5, 1H), 4.55 (dd, J=9.3, J=4.7, 1H), 5.82-5.86 (m, 1H), 6.50-6.53 (m, 1H), 6.85 (dd, J=8.2, J=1.2, 1H), 6.94 (s, 1H), 6.99 (t, J=7.9, 1H), 7.11-7.12 (m, 2H). LC/MS (method 1): $R_t$=2.03 min.; MS (ESIpos): m/z=332 [M+H]⁺.

Example 29A

Ethyl[8-chloro-1-2,3-dimethoxyphenyl)-4-oxo-1,2,4,5-tetrahydro-3H-3-benzazepin-3-yl]acetate

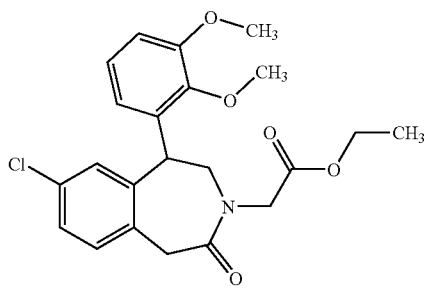

451 mg of the compound from Example 28A (1.36 mol) are dissolved in 8 ml of DMF, and 885 mg of caesium carbonate (2.72 mol) and 300 μl of ethyl bromoacetate (454 mg, 2.72 mol) are added. The reaction mixture is stirred at room temperature overnight. 10 ml of water are added, and the mixture is extracted three times with dichloromethane. The combined organic phases are washed with saturated sodium chloride solution and dried over sodium sulphate. The solvent is removed in a rotary evaporator, and the residue is purified by preparative HPLC (eluent: acetonitrile/water, gradient 20:80→95:5). 418 mg (30% of theory) of the title compound are obtained.

¹H-NMR (400 MHz, CDCl₃): δ=1.21 (t, J=7.1, 3H), 3.56-3.80 (m, 6H), 3.88 (s, 3H), 4.10-4.35 (m, 5H), 4.69-4.73 (m, 1H), 6.47-6.50 (m, 1H), 6.85 (dd, J=8.2, J=1.4, 1H), 6.94-7.01 (m, 2H), 7.08-7.14 (m, 2H). LC/MS (method 2): $R_t$=2.56 min.; MS (ESIpos): m/z=418 [M+H]⁺.

Example 30A

Ethyl[7-chloro-5-(2,3-dimethoxyphenyl)-1-isobutyl-2-oxo-1,2,4,5-tetrahydro-3H-3-benzazepin-3-yl]acetate

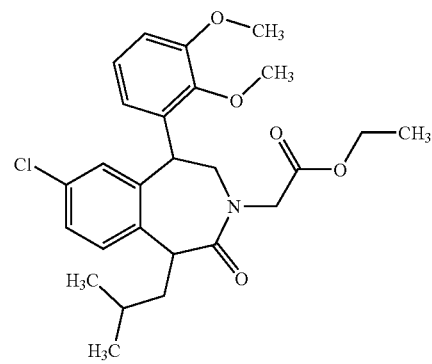

94 mg of the compound from Example 29A (0.22 mol) are dissolved in 0.90 ml of THF. At −78° C., 0.34 ml of a 1 M solution of 3-tert-butylimino-1,1,1,5,5,5-hexakis(dimethylamino)-3-(tris-(dimethylamino)phosphoranylidene)amino-1λ⁵,3λ⁵,5λ⁵-1,4-triphosphazadiene (P₄-t-Bu; 213 mg, 0.34 mol) in n-hexane is added drop wise, and the reaction solution is stirred at −78° C. for 30 min. 124 mg of 1-iodo-2-methylpropane (0.67 mol) are added drop wise, and the mixture is stirred at −78° C. for a further 2 h. The reaction solution is mixed with 1 N hydrochloric acid and water and extracted three times with dichloromethane. The combined organic phases are washed with saturated sodium bicarbonate solution, dried over sodium sulphate and concentrated in a rotary evaporator. The residue is purified by preparative HPLC (eluent: acetonitrile/water, gradient 20:80→95:5): 53 mg (50% of theory) of the title compound are obtained.

¹H-NMR (400 MHz, CDCl₃): δ=1.00 (d, J=6.6, 3H), 1.04 (d, J=6.4, 3H), 1.18 (t, J=7.1, 3H), 1.61-1.68 (m, 1H), 1.72-1.82 (m, 1H), 2.26-2.33 (m, 1H), 3.45-4.75 (m, 8H), 3.87 (s, 3H), 4.11 (q, J=7.1, 2H), 4.21 (d, J=17.4, 1H), 6.60-6.65 (m, 1H), 6.86 (d, J=8.1, 1H), 6.97-7.02 (m, 2H), 7.10-7.13 (m, 1H), 7.19 (d, J=8.3, 1H). LC/MS (method 3): $R_t$=3.12 min.; MS (ESIpos): m/z=474 [M+H]⁺.

Example 31A

Ethyl 1-[(7-chloro-1-isobutyl-2-oxo-5-{2-[(trimethylsilyl)ethynyl]phenyl}-1,2,4,5-tetrahydro-3H-3-benzazepin-3-yl)acetyl]piperidine-4-carboxylate

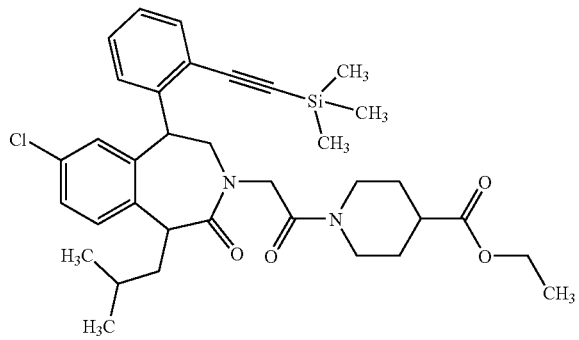

100 mg of the compound from Example 22 (0.166 mol) are dissolved in 6 ml of DMF/triethylamine (5:1). 12 mg of bis(triphenylphosphine)palladium(II) chloride (0.017 mol), 9 mg of copper(I) iodide (0.05 mol) and 183 mg of tetra-n-butylammonium iodide (0.497 mol) are added, and the reaction mixture is stirred at room temperature for 5 min. Then 94 μl of tri-methylsilylacetylene (65 mg, 0.662 mol) are added, and the mixture is stirred at 85° C. for 16 h. A further 12 mg of bis(triphenylphosphine)palladium(II) chloride (0.017 mol), 9 mg of copper(I) iodide (0.05 mol) and 188 μl of trimethylsilylacetylene (130 mg, 1.324 mol) are added, and the mixture is stirred at 85° C. for a further 16 h. A further 282 μl of trimethylsilylacetylene (195 mg, 1.986 mol) are added, and the mixture is again stirred at 85° C. for 16 h. For working up, the reaction mixture is mixed with dichloromethane, washed with 1 N hydrochloric acid and filtered through Celite, and the filtrate is concentrated in a rotary evaporator. The residue is purified by preparative HPLC (eluent: acetonitrile/water, gradient 20:80→95:5). 13 mg (12% of theory) of the title compound are obtained.

$^1$H-NMR (400 MHz, CDCl$_3$): δ=0.29 (s, 9H), 0.99-1.03 (m, 6H), 1.25 (t, J=7.1, 3H), 1.56-1.93 (m, 6H), 2.21-2.27 (m, 1H), 2.45-2.51 (m, 1H), 2.77-3.06 (m, 2H), 3.54-4.32 (m, 6H), 4.14 (t, J=7.1, 2H), 4.42-4.49 (m, 1H), 5.07-5.13 (m, 1H), 6.75 (br. s, 1H), 6.98 (s, 1H), 7.15-7.23 (m, 4H), 7.50-7.52 (m, 1H). LC/MS (method 1): R$_t$=3.27 min.; MS (ESIpos): m/z=621 [M+H]$^+$.

Exemplary Embodiments

Example 1

[7-Chloro-5-(2-chloroprene)-1-(2-methylallyl)-2-oxo-1,2,4,5-tetrahydrobenzo[d]azepin-3-yl]-acetic acid

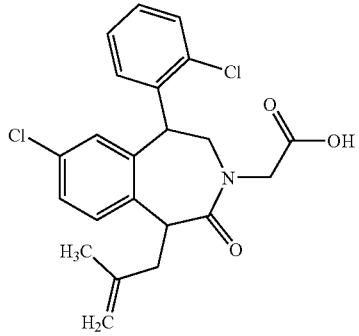

21 mg of the compound from Example 5A (0.05 mol) are dissolved in 1 ml of dioxane/water (1:1), and 70 μl of 1 M sodium hydroxide solution are added. The reaction mixture is stirred at room temperature for 24 h. 5 ml of 1 M hydrochloric acid are added, and the mixture is extrated three times with dichloromethane. The combined organic phases are dried over sodium sulphate and concentrated in a rotary evaporator. The residue is purified via preparative HPLC (eluent: acetonitrile/water with 0.1% formic acid, gradient 20:80→95:5). 11 mg (54% of theory) of the title compound are obtained.

$^1$H-NMR (400 MHz, CDCl$_3$): δ=2.69 (dd, J=16.0 und 6.5, 1H), 2.95 (dd, J=16.0 und 8.2, 1H), 3.78-4.06 (m, 2H), 4.09-4.29 (m, 2H), 4.64 (d, J=7.5, 1H), 4.71 (s, 1H), 4.87 (s, 1H), 5.07 (dd, 10.1 und 6.1, 1H), 6.79-6.85 (m, 1H), 6.93 (s, 1H), 7.14-7.27 (m, 4H), 7.41-7.46 (m, 1H). LC/MS (method 3): R$_t$=2.68 min.; MS (ESIpos): m/z=418 [M+H]$^+$.

Example 2

[7-Chloro-5-(2-chloroprene)-1-isobutyl-2-oxo-1,2,4,5-tetrahydrobenzo[d]azepin-3-yl]acetic acid

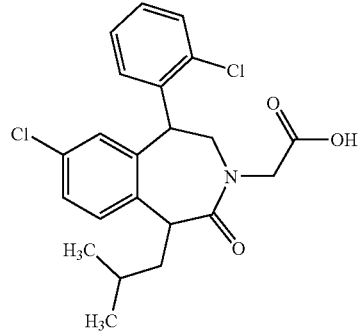

62 mg of the compound from Example 6A (0.14 mol) are dissolved in 1 ml of dioxane/water (1:1), and 210 μl of 1 M sodium hydroxide solution are added. The reaction mixture is stirred at room temperature overnight. 5 ml of 1 M hydrochloric acid are added, and the mixture is extrated three times with dichloromethane. The combined organic phases are dried over sodium sulphate and concentrated in a rotary evaporator. The residue is purified via preparative HPLC (eluent: acetonitrile/water with 0.1% formic acid, gradient 20:80→95:5). 49 mg (83% of theory) of the title compound are obtained.

LC/MS (method 1): R$_t$=2.65 min.; MS (ESIpos): m/z=420 [M+H]$^+$.

Example 3

Ethyl(1-{2-[7-chloro-5-(2-chloroprene)-1-isobutyl-2-oxo-1,2,4,5-tetrahydrobenzo[d]azepin-3-yl]-acetyl}piperidin-4-yl)acetate

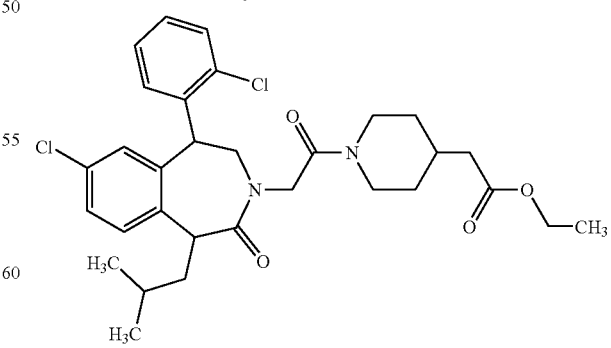

47 mg of the compound from Example 2 (0.11 mol) are dissolved in 2 ml of dichloromethane. 35 mg of ethyl 4-piperidylacetate hydrochloride (0.17 mol), 18 mg of 1-hydroxy-1H-benzo-triazole hydrate (0.13 mol), 26 mg of 1-ethyl-3-(3- dimethylaminopropyl)carbodiimide hydrochloride (0.13 mol) and 22 mg of N,N-diisopropylethylamine (0.17 mol) are added. The reaction mixture is stirred at room temperature overnight and then concentrated in a rotary evaporator, and the residue is purified by preparative HPLC (eluent: acetonitrile/water with 0.1% formic acid, gradient 20:80→95:5). 34 mg (53% of theory) of the title compound are obtained.

LC/MS (method 1): $R_t$=3.04 min.; MS (ESIpos): m/z=573 [M+H]$^+$.

Example 4

(1-{2-[7-Chloro-5-(2-chloroprene)-1-isobutyl-2-oxo-1,2,4,5-tetrahydrobenzo[d]azepin-3-yl]-acetyl}piperidin4-yl)acetic acid

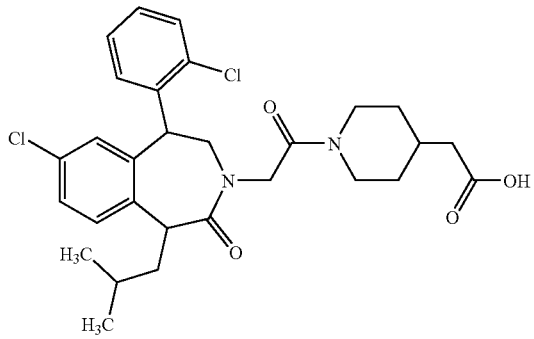

30 mg of the compound from Example 3 (0.05 mol) are dissolved in 1 ml of dioxane/water (1:1). 80 μl of 1 M sodium hydroxide solution are added, and the reaction mixture is stirred at room temperature overnight. It is acidified to pH 1 with 1 M hydrochloric acid and extracted three times with dichloromethane. The combined organic phases are dried over sodium sulphate, and the solvent is removed in a rotary evaporator. 25 mg (100% of theory) of the title compound are obtained.

LC/MS (method 1): $R_t$=2.76 min.; MS (ESIpos): m/z=545 [M+H]$^+$.

The enantiomers are separated by preparative HPLC on a chiral phase (Daicel Chiralpak AD-H 5 μm, column 250×20 mm; eluent: iso-hexane/ethanol 65:35; flow rate: 20 ml/min; detection: UV 220 nm):

Enantiomer 4-1:
$R_t$=10.2 min.
Enantiomer 4-2:
$R_t$=24.0 min.

Example 5

[5-(2-Chloroprene)-1-isobutyl-7-methyl-2-oxo-1,2,4,5-tetrahydrobenzo[d]azepin-3-yl]acetic acid

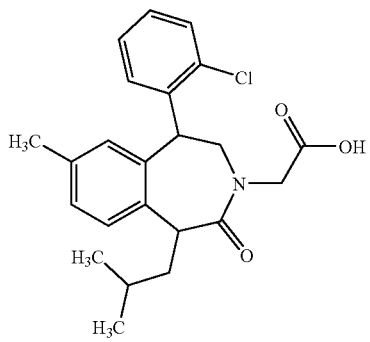

385 mg of the compound from Example 13A (0.90 mol) are dissolved in 12 ml of dioxane/water (1:1), and 3 ml of 1 N sodium hydroxide solution are added. The reaction mixture is stirred at room temperature for 3 h. It is diluted with water and acidified with 2 N hydrochloric acid, and the mixture is extracted three times with dichloromethane. The combined organic phases are dried over sodium sulphate and concentrated in a rotary evaporator. 355 mg (99% of theory) of the title compound are obtained.

$^1$H-NMR (400 MHz, CDCl$_3$): δ=1.00 (d, J=6.2, 3H), 1.01 (d, J=6.1, 3H), 1.70-1.83 (m, 2H), 2.15-2.24 (m, 1H), 2.19 (s, 3H), 3.96-4.14 (m, 3H), 4.34-4.41 (m, 1H), 4.98-5.01 (m, 1H), 6.71-6.77 (m, 2H), 7.01-7.04 (m, 1H), 7.11-7.21 (m, 3H), 7.40-7.43 (m, 1H). HPLC (method 6): $R_t$=5.11 min.

Example 6

[5-(2-Bromophenyl)-7-chloro-1-isobutyl-2-oxo-1,2,4,5-tetrahydrobenzo[d]azepin-3-yl]acetic acid

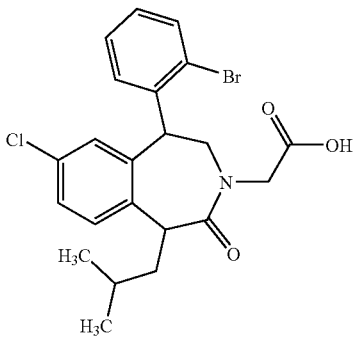

185 mg of the compound from Example 14A (0.38 mol) are dissolved in 6 ml of THF/methanol (1:1) and 1 ml of 1 N sodium hydroxide solution is added. The reaction mixture is stirred at room temperature for 16 h. It is diluted with water and acidified with 2 N hydrochloric acid, and the mixture is extracted three times with dichloromethane. The combined organic phases are dried over sodium sulphate and concentrated in a rotary evaporator. 172 mg (99% of theory) of the title compound are obtained.

$^1$H-NMR (400 MHz, CDCl$_3$): δ=1.00 (d, J=6.4, 3H), 1.01 (d, J=6.4, 3H), 1.67-1.82 (m, 2H), 2.19-2.26 (m, 1H), 3.95-4.09 (m, 2H), 4.18 (d, J=17.4, 1H), 4.38-4.46 (m, 1H), 5.02 (t, J=7.1, 1H), 6.73-6.79 (m, 1H), 6.91 (s, 1H), 7.10-7.23 (m, 4H), 7.61 (dd, J=7.9, J=1.1, 1H). HPLC (method 6): $R_t$=5.21 min.; MS (CI): m/z=464 [M+H]$^+$.

Example 7

Ethyl(1-{2-[5-(2-chloroprene)-1-isobutyl-7-methyl-2-oxo-1,2,4,5-tetrahydrobenzo[d]azepin-3-yl]-acetyl}piperidin-4-yl)acetate

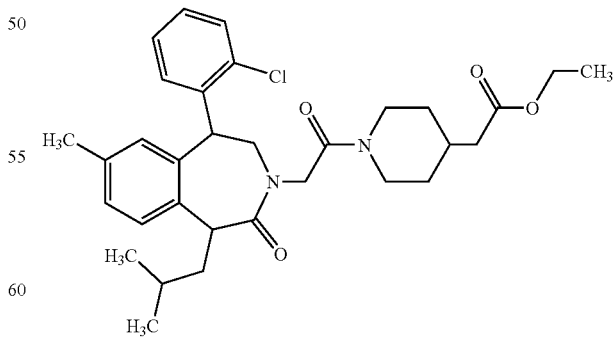

340 mg of the compound from Example 5 (0.85 mol) are dissolved in 5 ml of dimethylformamide, and 388 mg of O-(7-azabenzotriazol-1-yl)-N,N,N',N'-tetramethyluronium hexafluorophosphate (HATU) (1.02 mol) and 177 μl of diisopropylethylamine (132 mg, 1.02 mol) are added. After stirring at room temperature for 30 min, 212 mg of ethyl 4-piperidylacetate hydrochloride (1.02 mol) and a further 353 µl of diisopropylethylamine (264 mg, 2.04 mol) are added. The reaction mixture is stirred at room temperature overnight and then purified directly by preparative HPLC (eluent: acetonitrile/water with 0.1% formic acid, gradient 20:80→95:5). 300 mg (64% of theory) of the title compound are obtained.

HPLC (method 6): $R_t$=5.54 min.; MS (ESIpos): m/z=553 [M+H]$^+$.

Example 8

Ethyl(1-{2-[5-(2-bromophenyl)-7-chloro-1-isobutyl-2-oxo-1,2,4,5-tetrahydrobenzo[d]azepin-3-yl]-acetyl}piperidin-4-yl)acetate

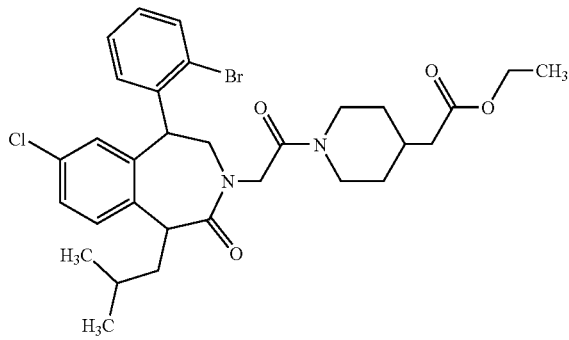

150 mg of the compound from Example 6 (0.32 mol) are dissolved in 2 ml of dimethylformamide, and 147 mg of O-(7-azabenzotriazol-1-yl)-N,N,N',N'-tetramethyluronium hexafluorophosphate (HATU) (0.39 mol) and 67 µl of diisopropylethylamine (50 mg, 0.39 mol) are added. After stirring at room temperature for 30 min, 80 mg of ethyl 4-piperidylacetate hydrochloride (0.39 mol) and a further 135 µl of diisopropylethylamine (100 mg, 0.77 mol) are added. The reaction mixture is stirred at room temperature overnight and then purified directly by preparative HPLC (eluent: acetonitrile/water with 0.1% formic acid, gradient 20:80→95:5). 130 mg (65% of theory) of the title compound are obtained.

LC/MS (method 3): $R_t$=3.24 min.; MS (ESIpos): m/z=618 [M+H]$^+$.

Example 9

(1-{2-[5-(2-Chloroprene)-1-isobutyl-7-methyl-2-oxo-1,2,4,5-tetrahydrobenzo[d]azepin-3-yl]-acetyl}piperidin-4-yl)acetic acid

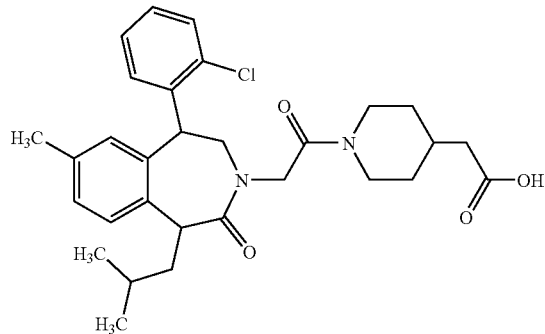

300 mg of the compound from Example 7 (0.54 mol) are dissolved in 6 ml of methanol. 1.5 ml of 2 N sodium hydroxide solution are added, and the reaction mixture is stirred at room temperature for 3 h. It is diluted with water, acidified to pH 1 with 1 N hydrochloric acid and extracted three times with dichloromethane. The combined organic phases are dried over sodium sulphate and the solvent is removed in a rotary evaporator. The residue is purified by preparative HPLC (eluent: acetonitrile/water with 0.1% formic acid, gradient 20:80→95:5). 200 mg (70% of theory) of the title compound are obtained.

HPLC (method 6): $R_t$=5.03 min.; MS (ESIpos): m/z=525 [M+H]$^+$.

Example 10

(1-{2-[5-2-Bromophenyl)-7-chloro-1-isobutyl-2-oxo-1,2,4,5-tetrahydrobenzo[d]azepin-3-yl]-acetyl}piperidin-4-yl)acetic acid

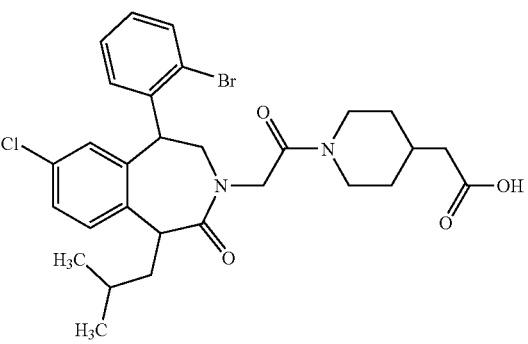

110 mg of the compound from Example 8 (0.18 mol) are dissolved in 6 ml of dioxane/methanol (1:1). 1.0 ml of 1 N sodium hydroxide solution is added, and the reaction mixture is stirred at room temperature for 3 h. It is diluted with water, acidified with 2 N hydrochloric acid and extracted three times with dichloromethane. The combined organic phases are dried over sodium sulphate, and the solvent is removed in a rotary evaporator. 105 mg (100% of theory) of the title compound are obtained.

HPLC (method 6): $R_t$=5.17 min.

Example 11

Ethyl(1-{2-[5-(2-chloroprene)-7-chloro-1-isobutyl-2-oxo-1,2,4,5-tetrahydrobenzo[d]azepin-3-yl]-acetyl}piperidin-4-yl)-carboxylate

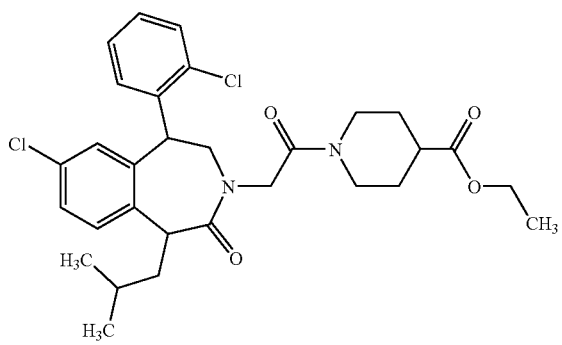

45 mg of the compound from Example 2 (0.11 mol) and 18 mg of ethyl piperidine-4-carboxylate (0.11 mol) are dissolved in 2 ml of dimethylformamide, and 21 mg of diethyl cyanophosphonate (0.12 mol) and 22 µl of triethylamine (16 mg, 0.16 mol) are added. The reaction mixture is stirred at room temperature overnight, then mixed with ethyl acetate and washed with 5% strength potassium bisulphate solution, saturated sodium bicarbonate solution and saturated sodium chloride solution. The organic phase is dried over sodium sulphate, the solvent is removed in a rotary evaporator, and the residue is purified by preparative HPLC (eluent: acetonitrile/water with 0.1% formic acid, gradient 20:80→95:5). 22 mg (36% of theory) of the title compound are obtained.

$^1$H-NMR (400 MHz, CDCl$_3$): δ=0.99 (d, J=6.2, 3H), 1.02 (d, J=6.4, 3H), 1.25 (t, J=7.1, 3H), 1.46-1.91 (m, 6H), 2.20-2.27 (m, 1H), 2.41-2.51 (m, 1H), 2.79-3.06 (m, 2H), 3.56-3.68 (m, 1H), 3.87-4.01 (m, 1H), 4.06-4.17 (m, 1H), 4.14 (t, J=7.1, 3H), 4.22-4.36 (m, 2H), 4.46-4.54 (m, 1H), 4.99-5.05 (m, 1H), 6.83-6.87 (m, 1H), 6.91-6.92 (m, 1H), 7.14-7.22 (m, 4H), 7.40-7.42 (m, 1H). LC/MS (method 3): R$_t$=3.15 min.; MS (ESIpos): m/z=559 [M+H]$^+$.

Example 12

(1-{2-[5-2-Chloroprene)-7-chloro-1-isobutyl-2-oxo-1,2,4,5-tetrahydrobenzo[d]azepin-3-yl]-acetyl}piperidin-4-yl)carboxylic acid

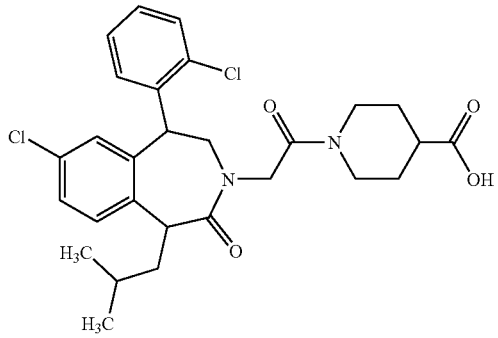

18 mg of the compound from Example 11 (0.11 mol) are dissolved in dioxane/water (2:1), mixed with 50 μl of 1 N sodium hydroxide solution and stirred at room temperature overnight. The reaction solution is acidified (pH 2) with 1 N hydrochloric acid and stirred for 20 min, the product separating out as precipitate. The precipitate is filtered off and dried under high vacuum. 11.7 mg (65% of theory) of the title compound are obtained.

$^1$H-NMR (400 MHz, CDCl$_3$): δ=0.99 (d, J=6.1, 3H), 1.02 (d, J=6.4, 3H), 1.54-1.97 (m, 6H), 2.20-2.27 (m, 1H), 2.48-2.56 (m, 1H), 2.80-2.89 (m, 1H), 2.93-3.05 (m, 1H), 3.58-3.70 (m, 1H), 3.85-4.53 (m, 6H), 5.00-5.05 (m, 1H), 6.82-6.89 (m, 1H), 6.92 (s, 1H), 7.15-7.22 (m, 4H), 7.39-7.42 (m, 1H). LC/MS (method 2): R$_t$=2.70 min.; MS (ESIpos): m/z=531 [M+H]$^+$.

Example 13

Methyl 4-{2-[7-chloro-5-(2-chloroprene)-1-isobutyl-2-oxo-1,2,4,5-tetrahydrobenzo[d]azepin-3-yl]acetylamino}hexanoate

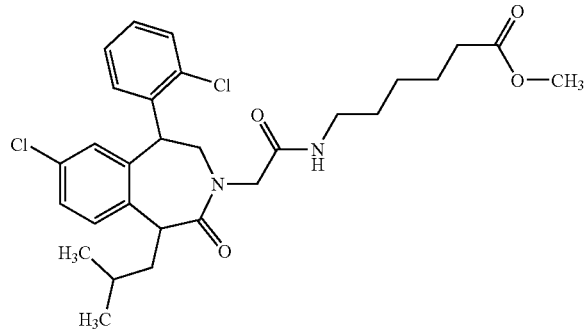

45 mg of the compound from Example 2 (0.11 mol) and 20 mg of methyl 6-aminohexanoate hydrochloride (0.11 mol) are dissolved in 2 ml of dimethylformamide, and 21 mg of diethyl cyanophosphonate (0.12 mol) and 40 μl of triethylamine (27 mg, 0.27 mol) are added. The reaction mixture is stirred at room temperature overnight, then mixed with ethyl acetate and washed with 5% strength potassium bisulphate solution, saturated sodium bicarbonate solution and saturated sodium chloride solution. The organic phase is dried over sodium sulphate, the solvent is removed in a rotary evaporator, and the residue is purified by preparative HPLC (eluent: acetonitrile/water with 0.1% formic acid, gradient 20:80→95:5). 36 mg (62% of theory) of the title compound are obtained.

$^1$H-NMR (400 MHz, CDCl$_3$): δ=1.00 (d, J=6.2, 3H), 1.03 (d, J=6.2, 3H), 1.15-1.36 (m, 5H), 1.50-1.62 (m, 2H), 1.69-1.79 (m, 2H), 2.17-2.27 (m, 1H), 2.26 (t, J=7.6, 2H), 3.01-3.20 (m, 2H), 3.65 (s, 3H), 3.89-3.99 (m, 1H), 4.14-4.23 (m, 1H), 4.22 (d, J =15.1, 1H), 4.46-4.51 (m, 1H), 5.01 (dd, J=10.2, J=6.4, 1H), 5.92-5.98 (m, 1H), 6.81-6.85 (m, 1H), 6.93 (s, 1H), 7.14-7.24 (m, 4H), 7.42 (dd, J=7.6, J=1.9, 1H). LC/MS (method 3): R$_t$=3.04 min.; MS (ESIpos): m/z=547 [M+H]$^+$.

Example 14

4-{2-[7-Chloro-5-(2-chloroprene)-1-isobutyl-2-oxo-1,2,4,5-tetrahydrobenzo[d]azepin-3-yl]-acetylamino}hexanoic acid

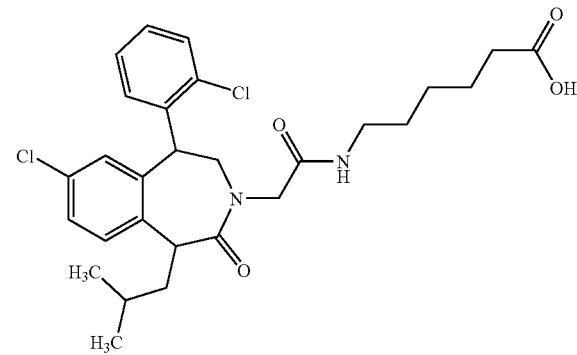

32 mg of the compound from Example 13 (0.06 mol) are dissolved in dioxane/water (2:1), mixed with 90 μl of 1 N sodium hydroxide solution and stirred at room temperature overnight. The reaction solution is acidified (pH 2) with 1 N hydrochloric acid and extracted three times with dichloromethane. The combined organic phases are dried over sodium sulphate, and the solvent is removed in a rotary evaporator. 27 mg (88% of theory) of the title compound are obtained.

$^1$H-NMR (400 MHz, CDCl$_3$): δ=1.00 (d, J=6.1, 3H), 1.02 (d, J=6.1, 3H), 1.18-1.38 (m, 5H), 1.58 (sept, J=7.3, 2H), 1.68-1.78 (m, 2H), 2.20-2.24 (m, 1H), 2.23 (t, J=7.3, 2H), 3.04-3.20 (m, 2H), 3.91-4.02 (m, 1H), 4.15-4.24 (m, 1H), 4.24 (d, J=14.9, 1H), 4.47-4.53 (m, 1H), 4.99-5.04 (m, 1H), 6.01-6.05 (m, 1H), 6.81-6.86 (m, 1H), 6.93 (s, 1H), 7.16-7.23

(m, 4H), 7.42 (dd, J=7.6, J=1.5, 1H). LC/MS (method 3): R$_t$=2.68 min.; MS (ESIpos): m/z=533 [M+H]$^+$.

Example 15

[7-Chloro-1-isobutyl-5-(2-methoxyphenyl)-2-oxo-1,2,4,5-tetrahydro-3H-3-benzazepin-3-yl]acetic acid

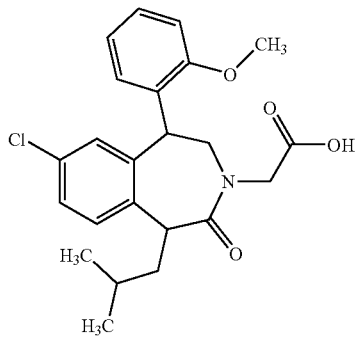

85 mg of the compound from Example 23A (0.19 mol) are dissolved in 3.5 ml of dioxane/water (1:1) and mixed with 0.29 ml of 1 N sodium hydroxide solution (0.29 mol). The reaction mixture is stirred at room temperature for 3 h. It is acidified with 5 ml of 1 N hydrochloric acid, and the mixture is extracted three times with dichloromethane. The combined organic phases are dried over sodium sulphate and concentrated in a rotary evaporator. 80 mg (100% of theory) of the title compound are obtained.

$^1$H-NMR (400 MHz, CDCl$_3$): δ=0.99-1.02 (m, 6H), 1.64-1.80 (m, 2H), 2.20-2.27 (m, 1H), 3.81-3.89 (m, 1H), 3.83 (s, 3H), 4.08-4.23 (m, 3H), 4.48-4.53 (m, 1H), 4.80 (dd, J=9.5, J=6.2, 1H), 6.75-6.79 (m, 1H), 6.86-9.94 (m, 3H), 7.12-7.17 (m, 2H), 7.23-7.27 (m, 1H). LC/MS (method 1): R$_t$=2.49 min.; MS (ESIpos): m/z=416 [M+H]$^+$.

Example 16

Ethyl 1-{[7-chloro-1-isobutyl-5-2-methoxyphenyl)-2-oxo-1,2,4,5-tetrahydro-3H-3-benzazepin-3-yl]acetyl}piperidine-4-carboxylate

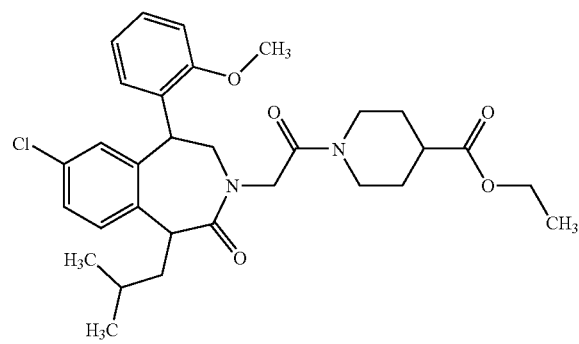

53 mg of the compound from Example 15 (0.13 mol) and 21 mg of ethyl piperidine-4-carboxylate (0.13 mol) are dissolved in 1.9 ml of dimethylformamide, and 25 mg of diethyl cyanophosphonate (0.14 mol) and 30 µl of triethylamine (19 mg, 0.19 mol) are added. The reaction mixture is stirred at room temperature overnight, mixed with ethyl acetate and washed with 5% strength potassium bisulphate solution, saturated sodium bicarbonate solution and saturated sodium chloride solution. The organic phase is dried over sodium sulphate, the solvent is removed in a rotary evaporator, and the residue is purified by preparative HPLC (eluent: acetonitrile/water, gradient 20:80→95:5). 52 mg (74% of theory) of the title compound are obtained.

$^1$H-NMR (400 MHz, DMSO-d$_6$): δ=0.95-0.99 (m, 6H), 1.17 (t, J=7.3, 3H), 1.29-1.67 (m, 4H), 1.77-1.81 (m, 2H), 2.10-2.17 (m, 1H), 2.54-2.59 (m, 1H), 2.67-2.75 (m, 1H), 2.99-3.06 (m, 1H), 3.41-3.47 (m, 1H), 3.65-3.71 (m, 1H), 3.68 (s, 3H), 4.02-4.39 (m, 4H), 4.06 (t, J=7.3, 2H), 4.69-4.77 (m, 2H), 6.89 (s, 1H), 6.93 (t, J=7.4, 1H), 7.01 (d, J=8.2, 1H), 7.11-7.19 (m, 3H), 7.25-7.29 (m, 1H). LC/MS (method 3): R$_t$=3.04 min.; MS (ESIpos): m/z=555 [M+H]$^+$.

Example 17

7-Chloro-1-isobutyl-5-(2-methoxyphenyl)-3-(2-oxo-2-piperidin-1-ylethyl-1,3,4,5-tetrahydro-2H-3-benzazepin-2-one

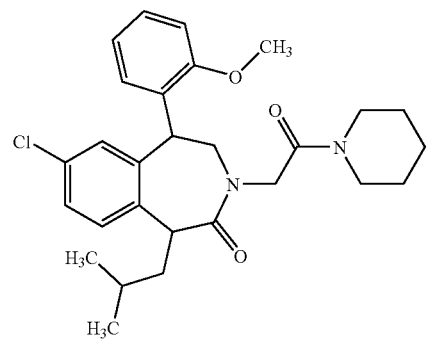

25 mg of the compound from Example 15 (0.06 mol) and 6 mg of piperidine (0.06 mol) are dissolved in 1.0 ml of dimethylformamide, and 12 mg of diethyl cyanophosphonate (0.07 mol) and 13 µl of triethylamine (9 mg, 0.09 mol) are added. The reaction mixture is stirred at room temperature overnight, then mixed with ethyl acetate and washed with 5% strength potassium bisulphate solution, saturated sodium bicarbonate solution and saturated sodium chloride solution. The organic phase is dried over sodium sulphate, the solvent is removed in a rotary evaporator, and the residue is purified by preparative HPLC (eluent: acetonitrile/water, gradient 20:80→95:5). 16 mg (54% of theory) of the title compound are obtained.

$^1$H-NMR (400 MHz, CDCl$_3$): δ=0.99 (d, J=6.4, 3H), 1.03 (d, J=6.5, 3H), 1.41-1.62 (m, 6H), 1.63-1.80 (m, 2H), 2.24-2.31 (m, 1H), 3.20-3.25 (m, 2H), 3.45-3.52 (m, 2H), 3.78 (s, 3H), 3.79-4.34 (m, 4H), 4.64 (br. s, 1H), 4.76 (dd, J=10.6,

J=7.0, 1H), 6.86-6.95 (m, 4H), 7.10-7.25 (m, 3H). LC/MS (method 2): R$_t$=3.04 min.; MS (ESIpos): m/z=483 [M+H]$^+$.

Example 18

1-{[7-Chloro-1-isobutyl-5-(2-methoxyphenyl)-2-oxo-1,2,4,5-tetrahydro-3H-3-benzazepin-3-yl]-acetyl}piperidine-4-carboxylic acid

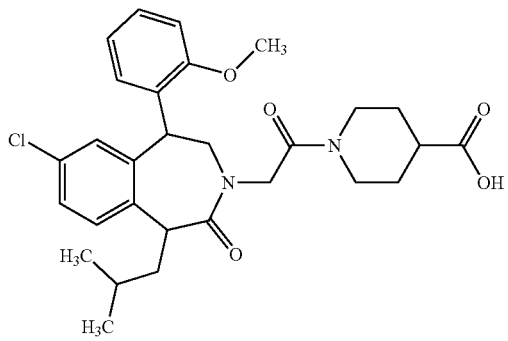

46 mg of the compound from Example 16 (0.08 mol) are dissolved in 2.5 ml of dioxane/water (2:1), mixed with 120 µl of 1 N sodium hydroxide solution and stirred at room temperature overnight. The reaction solution is acidified (pH 2) with 1 N hydrochloric acid and extracted three times with dichloromethane. The combined organic phases are dried over sodium sulphate and concentrated in a rotary evaporator, and the residue is purified by preparative HPLC (eluent: acetonitrile/water with 0.1% formic acid, gradient 20:80→95:5). 30 mg (69% of theory) of the title compound are obtained.

$^1$H-NMR (400 MHz, CDCl$_3$): δ=0.99 (d, J=6.4, 3H), 1.02 (d, J=6.4, 3H), 1.51-1.83 (m, 5H), 1.89-1.96 (m, 1H), 2.23-2.30 (m, 1H), 2.47-2.52 (m, 1H), 2.79-3.03 (m, 2H), 3.62-4.43 (m, 6H), 3.78 (s, 3H), 4.60-4.64 (m, 1H), 4.73-4.77 (m, 1H), 6.86-6.95 (m, 4H), 7.09-7.25 (m, 3H). LC/MS (method 2): R$_t$=2.61 min.; MS (ESIpos): m/z=527 [M+H]$^+$.

Example 19

[7-Chloro-5-2,3-dimethoxyphenyl)-1-isobutyl-2-oxo-1,2,4,5-tetrahydro-3H-3-benzazepin-3-yl]acetic acid

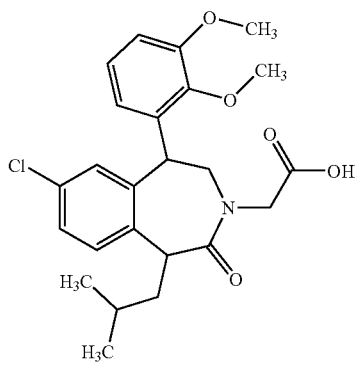

73 mg of the compound from Example 30A (0.15 mol) are dissolved in 3.5 ml of dioxane/water (1:1), and 0.23 ml of 1 N sodium hydroxide solution (0.23 mol) is added. The reaction mixture is stirred at room temperature for 3 h. It is acidified with 5 ml of 1 N hydrochloric acid, and the mixture is extracted three times with dichloromethane. The combined organic phases are dried over sodium sulphate and concentrated in a rotary evaporator. 69 mg (100% of theory) of the title compound are obtained.

$^1$H-NMR (400 MHz, DMSO-d$_6$): δ=0.96 (d, J=6.2, 3H), 0.98 (d, J=6.2, 3H), 1.54-1.68 (m, 2H), 2.08-2.16 (m, 1H), 3.25 (s, 3H), 3.42-3.56 (m, 1H), 3.79 (s, 3H), 4.01-4.14 (m, 2H), 4.33-4.42 (m, 1H), 4.69 (dd, J=12.0, J=7.1, 1H), 4.74-4.79 (m, 1H), 6.81-6.84 (m, 1H), 6.92 (s, 1H), 6.98-7.09 (m, 2H), 7.20-7.23 (m, 2H), 12.55 (br. s, 1H). LC/MS (method 2): R$_t$=2.67 min.; MS (ESIpos): m/z=446 [M+H]$^+$.

Example 20

Ethyl 1-{[7-chloro-5-(2,3-dimethoxyphenyl)-1-isobutyl-2-oxo-1,2,4,5-tetrahydro-3H-3-benzazepin-3-yl]acetyl}piperidine-4-carboxylate

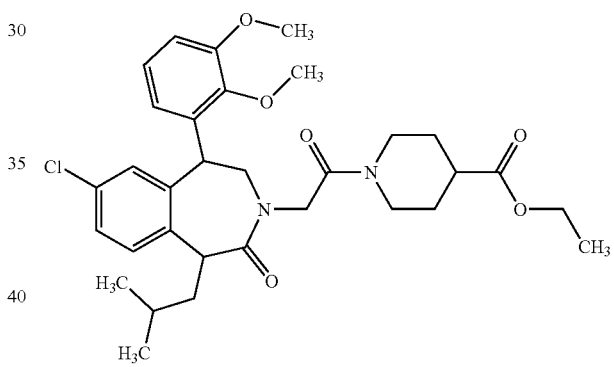

69 mg of the compound from Example 19 (0.15 mol) and 26 mg of ethyl piperidine-4-carboxylate (0.16 mol) are dissolved in 2.5 ml of dimethylformamide, and 30 mg of diethyl cyanophosphonate (0.17 mol) and 32 µl of triethylamine (23 mg, 0.23 mol) are added. The reaction mixture is stirred at room temperature overnight, then mixed with ethyl acetate and washed with 5% strength potassium bisulphate solution, saturated sodium bicarbonate solution and saturated sodium chloride solution. The organic phase is dried over sodium sulphate, the solvent is removed in a rotary evaporator, and the residue is purified by preparative HPLC (eluent: acetonitrile/water, gradient 20:80→95:5). 62 mg (68% of theory) of the title compound are obtained.

$^1$H-NMR (400 MHz, CDCl$_3$): δ=1.00 (d, J=6.2, 3H), 1.04 (d, J=6.2, 3H), 1.24 (t, J=7.1, 3H), 1.29-1.94 (m, 6H), 2.23-2.35 (m, 1H), 2.39-2.49 (m, 1H), 2.76-3.07 (m, 2H), 3.43 (s, 3H), 3.53-4.55 (m, 6H), 3.86 (m, 3H), 4.13 (q, J=7.1, 2H), 4.57-4.66 (m, 1H), 4.73-4.83 (m, 1H), 6.67-6.71 (m, 1H), 6.84-6.87 (m, 1H), 6.96-7.20 (m, 4H). LC/MS (method 3): R$_t$=3.04 min.; MS (ESIpos): m/z=585 [M+H]$^+$.

Example 21

1-{[7-Chloro-5-(2,3-dimethoxyphenyl)-1-isobutyl-2-oxo-1,2,4,5-tetrahydro-3H-3-benzazepin-3-yl]-acetyl}piperidine-4-carboxylic acid

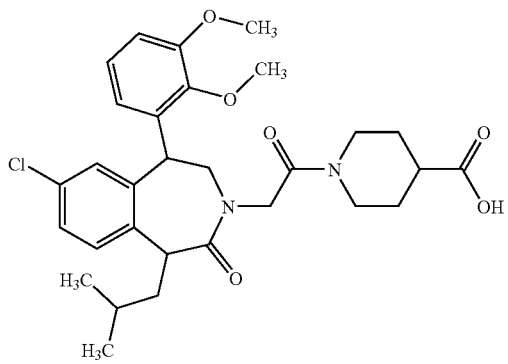

64 mg of the compound from Example 20 (0.11 mol) are dissolved in 3.3 ml of dioxane/water (2:1), mixed with 165 µl of 1 N sodium hydroxide solution and stirred at room temperature overnight. The reaction solution is acidified (pH 2) with 1 N hydrochloric acid and extracted three times with dichloromethane. The combined organic phases are dried over sodium sulphate and concentrated in a rotary evaporator, and the residue is purified by preparative HPLC (eluent: acetonitrile/water with 0.1% formic acid, gradient 20:80→95:5). 61 mg (100% of theory) of the title compound are obtained.

$^1$H-NMR (400 MHz, CDCl$_3$): δ=1.00 (d, J=6.5, 3H), 1.04 (d, J=6.4, 3H), 1.48-1.97 (m, 6H), 2.26-2.32 (m, 1H), 2.46-2.52 (m, 1H), 2.77-3.04 (m, 2H), 3.43 (s, 3H), 3.54-4.63 (m, 7H), 3.86 (s, 3H), 4.76-4.81 (m, 1H), 6.67-7.20 (m, 6H). LC/MS (method 2): R$_t$=2.61 min.; MS (ESIpos): m/z=557 [M+H]$^+$.

Example 22

Ethyl 1-{[5-(2-bromophenyl)-7-chloro-1-isobutyl-2-oxo-1,2,4,5-tetrahydro-3H-3-benzazepin-3-yl]-acetyl}piperidin-4-carboxylate

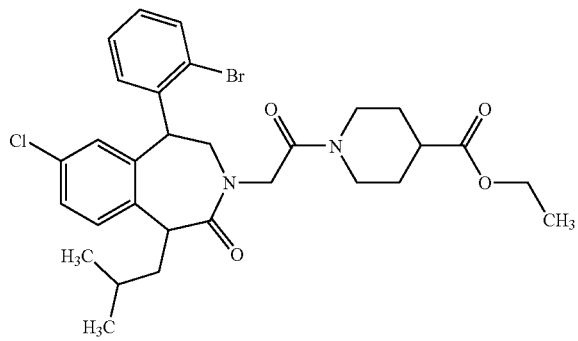

190 mg of the compound from Example 6 (0.39 mol) and 65 mg of ethyl piperidine-4-carboxylate (0.41 mol) are dissolved in 5.0 ml of dimethylformamide, and 75 mg of diethyl cyanophosphonate (0.43 mol) and 81 µl of triethylamine (59 mg, 0.58 mol) are added. The reaction mixture is stirred at room temperature for 2.5 h, then mixed with ethyl acetate and washed with 5% strength potassium bisulphate solution, saturated sodium bicarbonate solution and saturated sodium chloride. The organic phase is dried over sodium sulphate, the solvent is removed in a rotary evaporator, and the residue is purified by preparative HPLC (eluent: acetonitrile/water, gradient 20:80→95:5). 204 mg (87% of theory) of the title compound are obtained.

$^1$H-NMR (400 MHz, CDCl$_3$): δ=1.00 (d, J=6.2, 3H), 1.03 (d, J=6.2, 3H), 1.25 (t, J=7.1, 3H), 1.46-1.93 (m, 6H), 2.20-2.28 (m, 1H), 2.44-2.51 (m, 1H), 2.80-3.07 (m, 2H), 3.55-4.33 (m, 6H), 4.14 (t, J=7.1, 2H), 4.47-4.54 (m, 1H), 4.99-5.05 (m, 1H), 6.82-6.86 (m, 1H), 6.92 (br. s, 1H), 7.09-7.24 (m, 4H), 7.59-7.61 (m, 1H). LC/MS (method 3): R$_t$=3.16 min.; MS (ESIpos): m/z=603 [M+H]$^+$.

Example 23

1-{[5-(2-Bromophenyl)-7-chloro-1-isobutyl-2-oxo-1,2,4,5-tetrahydro-3H-3-benzazepin-3-yl]acetyl}piperidine-4-carboxylic acid

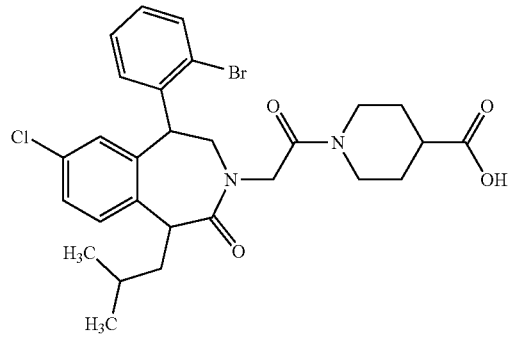

24 mg of the compound from Example 22 (0.04 mol) are dissolved in 2.0 ml of THF/methanol (1:1). 0.1 ml of 1 N sodium hydroxide solution is added, and the reaction mixture is stirred at room temperature for 16 h. It is diluted with water and acidified with 1 N hydrochloric acid, and the mixture is extracted three times with dichloromethane. The combined organic phases are dried over sodium sulphate, and the solvent is removed in a rotary evaporator. 23 mg (100% of theory) of the title compound are obtained.

$^1$H-NMR (400 Mz, CDCl$_3$): δ=1.00 (d, J=6.2, 3H), 1.02 (d, J=6.2, 3H), 1.41-1.98 (m, 6H), 2.19-2.27 (m, 1H), 2.49-2.56 (m, 1H), 2.81-3.06 (m, 2H), 3.56-4.43 (m, 6H), 4.47-4.54 (m, 1H), 4.98-5.04 (m, 1H), 6.79-6.85 (m, 1H), 6.91 (br. s, 1H), 7.09-7.25 (m, 4H), 7.60 (dd, J=7.9, J=1.1, 1H). LC/MS (method 3): R$_t$=2.75 min.; MS (ESIpos): m/z=575 [M+H]$^+$.

Example 24

1-{[7-Chloro-5-(2-ethynylphenyl)-1-isobutyl-2-oxo-1,2,4,5-tetrahydro-3H-3-benzazepin-3-yl]-acetyl}piperidine-4-carboxylic acid

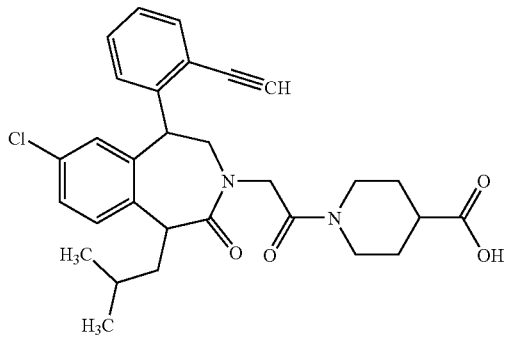

12 mg of the compound from Example 31A (0.019 mol) are dissolved in 2.0 ml of THF/methanol (1:1), mixed with 100 μl of 1 N sodium hydroxide solution and stirred at room temperature for 16 h. The reaction solution is acidified with 1 N hydrochloric acid, diluted with water and extracted three times with dichloromethane. The combined organic phases are dried over sodium sulphate, and the residue is purified by preparative HPLC (eluent: acetonitrile/water with 0.1% formic acid, gradient 20:80→95:5). 6 mg (58% of theory) of the title compound are obtained.

LC/MS (method 1): $R_t$=2.47 min.; MS (ESIpos): m/z=521 [M+H]$^+$.

The following compounds are prepared in analogy to the examples described above from the appropriate starting compounds:

Example 25

(1-{2-[7-Chloro-1-isobutyl-5-(2-methoxyphenyl)-2-oxo-1,2,4,5-tetrahydrobenzo[d]azepin-3-yl]-acetyl}piperidin4-yl)acetic acid

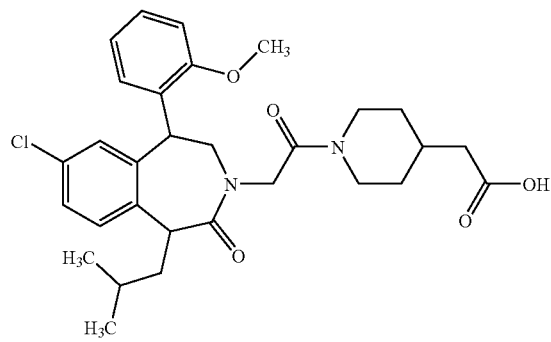

Example 26

(1-{2-[7-Chloro-5-(2,4-dimethylphenyl)-1-isobutyl-2-oxo-1,2,4,5-tetrahydrobenzo[d]azepin-3-yl]-acetyl}piperidin-4-yl)acetic acid

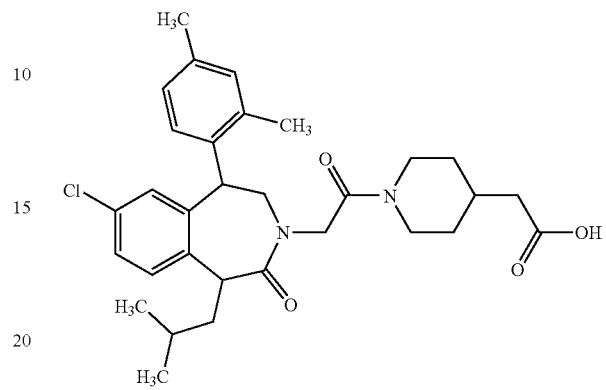

Example 27

(1-{2-[7-Chloro-5-(2,3-dimethylphenyl)-1-isobutyl-2-oxo-1,2,4,5-tetrahydrobenzo[d]azepin-3-yl]-acetyl}piperidin-4-yl)acetic acid

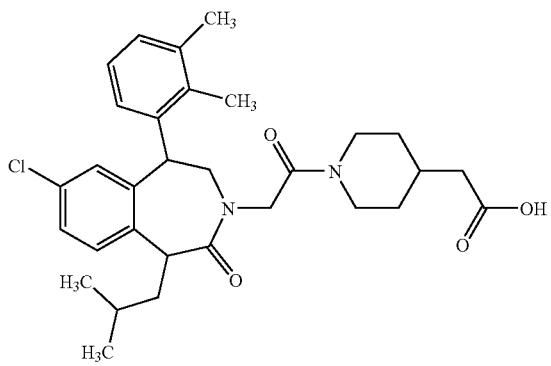

Example 28

(1-{2-[7-Chloro-5-2,3-dimethoxyphenyl)-1-isobutyl-2-oxo-1,2,4,5-tetrahydrobenzo[d]azepin-3-yl]-acetyl}piperidin-4-yl)acetic acid

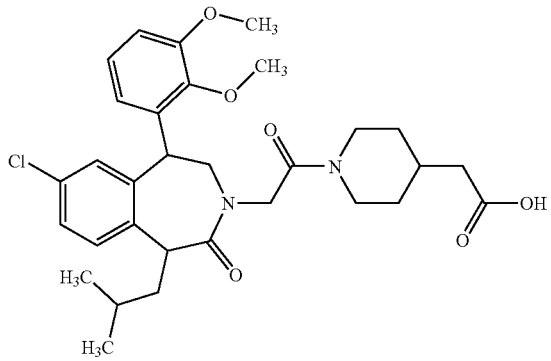

Example 29

(1-{2-[7-Chloro-5-(2,3-dihydrobenzo[1,4]dioxin-5-yl)-1-isobutyl-2-oxo-1,2,4,5-tetrahydrobenzo-[d]azepin-3-yl]-acetyl}piperidin-4-yl)acetic acid

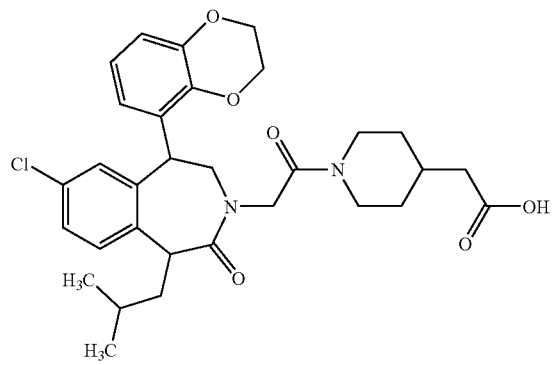

Example 30

(1-{2-[7-Chloro-1-isobutyl-5-(naphthalene-1-yl)-2-oxo-1,2,4,5-tetrahydrobenzo[d]azepin-3-yl]-acetyl}piperidin-4-yl)acetic acid

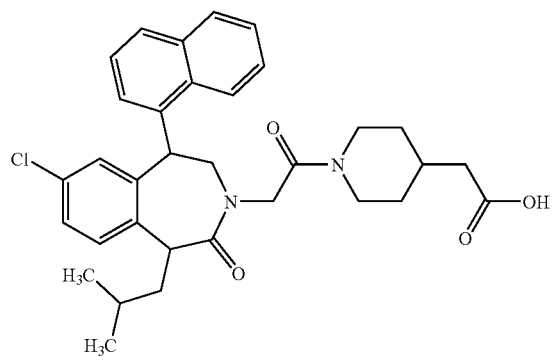

Example 31

(1-{2-[5-2-Chloroprene)-1-isobutyl-7-methyl-2-oxo-1,2,4,5-tetrahydrobenzo[d]azepin-3-yl]-acetyl}piperidin4-yl)acetic acid

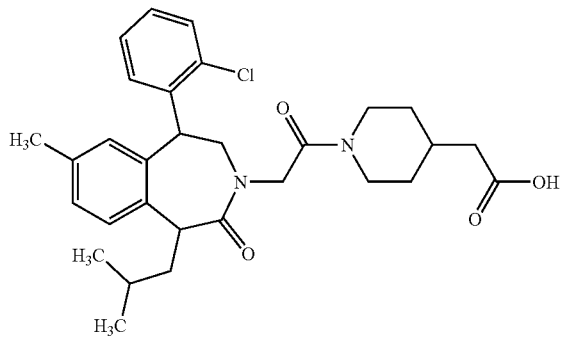

Example 32

(1-{2-[5-2-Chloroprene)-1-isobutyl-2-oxo-7-trifluoromethyl-1,2,4,5-tetrahydrobenzo[d]azepin-3-yl]acetyl}piperidin-4-yl)acetic acid

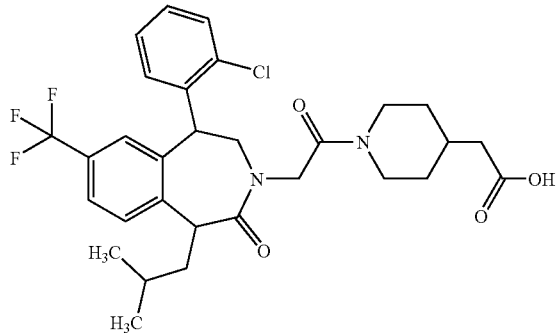

Example 33

(1-{2-[5-2-Chloroprene)-1-(2,2-dimethylpropyl)-2-oxo-7-trifluoromethyl-1,2,4,5-tetrahydrobenzo[d]azepin-3-yl]acetyl}piperidin-4-yl)acetic acid

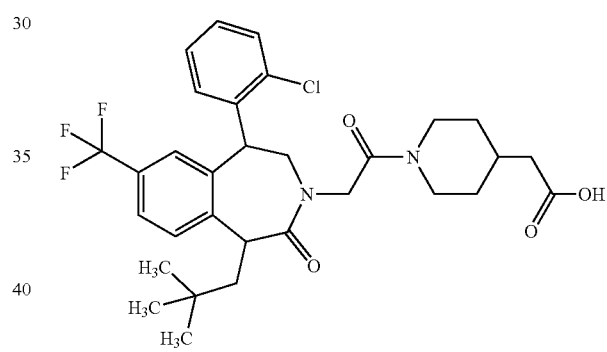

Example 34

(1-{2-[1-Isobutyl-5-(2-methoxyphenyl)-2-oxo-7-trifluoromethyl-1,2,4,5-tetrahydrobenzo[d]azepin-3-yl]acetyl}piperidin-4-yl)acetic acid

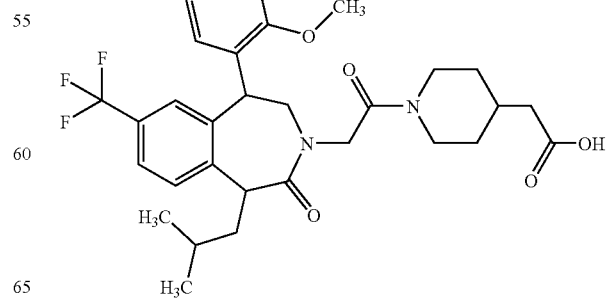

Example 35

(1-{2-[1-(2,2-Dimethylpropyl)-5-(2-methoxyphenyl)-2-oxo-7-trifluoromethyl-1,2,4,5-tetrahydrobenzo[d]azepin-3-yl]acetyl}piperidin-4-yl)acetic acid

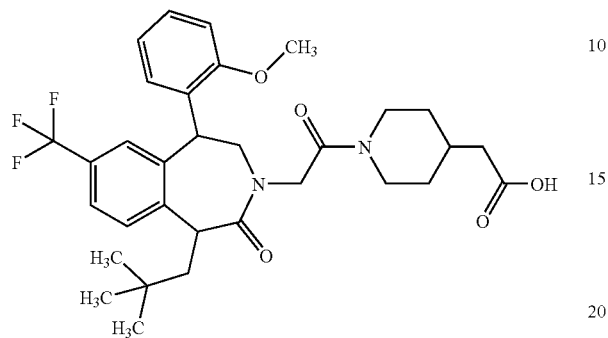

Example 36

(1-{2-[5-(2,3-Dimethoxyphenyl)-1-isobutyl-2-oxo-7-trifluoromethyl-1,2,4,5-tetrahydrobenzo[d]-azepin-3-yl]acetyl}piperidin-4-yl)acetic acid

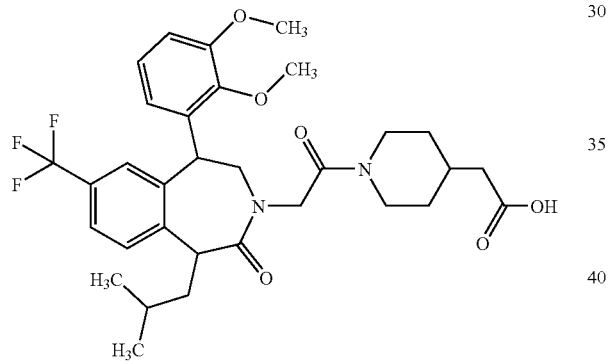

Example 37

(1-{2-[5-(2,3-Dimethoxyphenyl)-1-(2,2-dimethylpropyl)-2-oxo-7-trifluoromethyl-1,2,4,5-tetrahydrobenzo[d]azepin-3-yl]acetyl}piperidin-4-yl)acetic acid

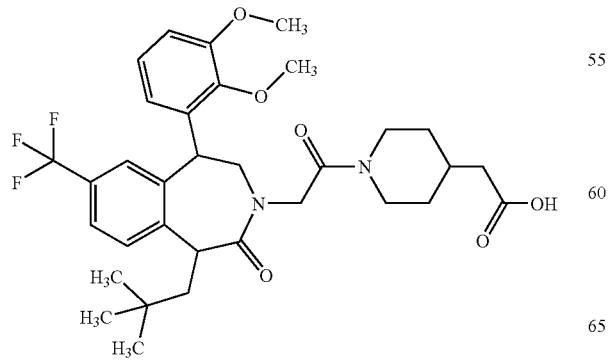

Example 38

{2-[7-Chloro-5-(2-chloroprene)-1-isobutyl-2-oxo-1,2,4,5-tetrahydrobenzo[d]azepin-3-yl]acetylamino}acetic acid

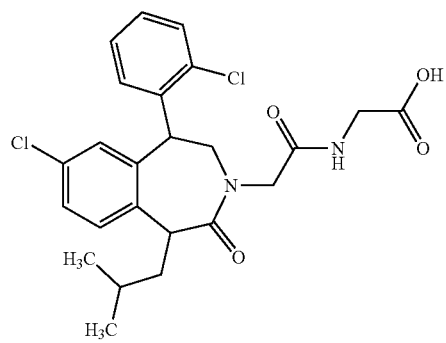

Example 39

4-{2-[7-Chloro-5-(2-chloroprene)-1-isobutyl-2-oxo-1,2,4,5-tetrahydrobenzo[d]azepin-3-yl]-acetylamino}butyric acid

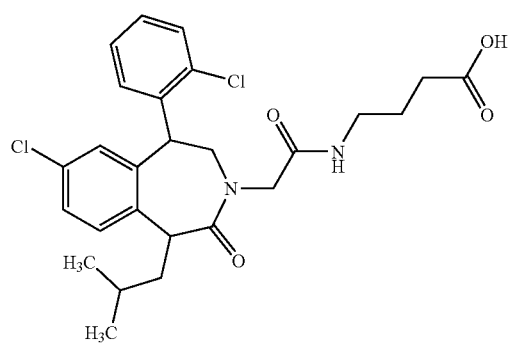

Example 40

(1-{2-[7-Chloro-5-(2-chloroprene)-1-(2,2-dimethylpropyl)-2-oxo-1,2,4,5-tetrahydrobenzo[d]azepin-3-yl]acetyl}piperidin-4-yl)carboxylic acid

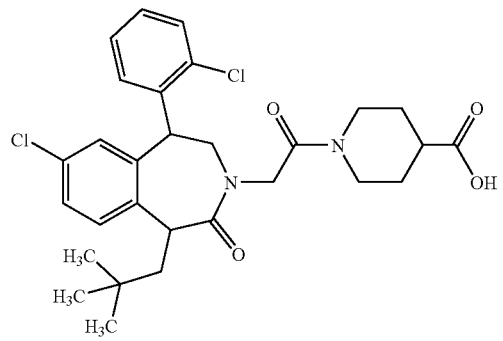

Example 41

(1-{2-[7-Chloro-1-(2,2-dimethylpropyl)-5-(2-methoxyphenyl)-2-oxo-1,2,4,5-tetrahydrobenzo[d]-azepin-3-yl]acetyl}piperidin-4-yl)carboxylic acid

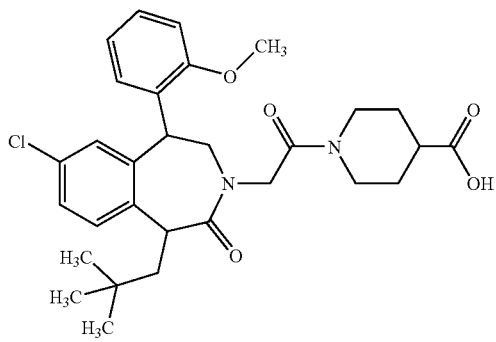

Example 42

(1-{2-[7-Chloro-5-(2,4-dimethylphenyl)-1-isobutyl-2-oxo-1,2,4,5-tetrahydrobenzo[d]azepin-3-yl]-acetyl}piperidin-4-yl)carboxylic acid

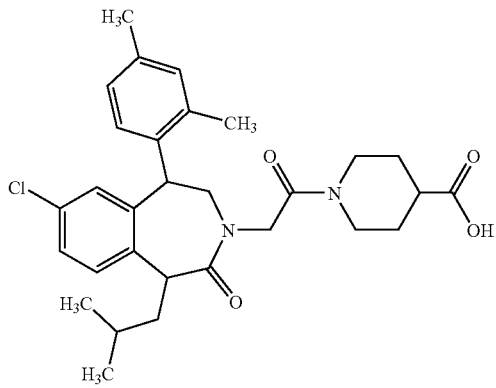

Example 43

(1-{2-[7-Chloro-5-(2,3-dimethylphenyl)-1-isobutyl-2-oxo-1,2,4,5-tetrahydrobenzo[d]azepin-3-yl]-acetyl}piperidin-4-yl)carboxylic acid

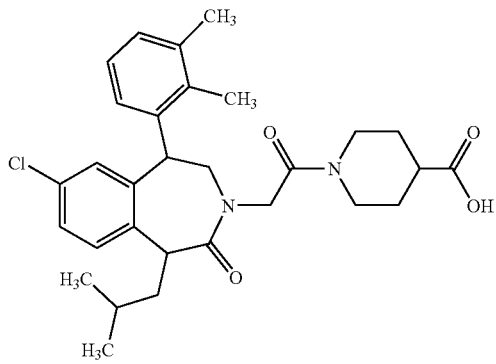

Example 44

(1-{2-[7-Chloro-5-(2,3-dimethoxyphenyl)-1-(2,2-dimethylpropyl)-2-oxo-1,2,4,5-tetrahydrobenzo-[d]azepin-3-yl]acetyl}piperidin-4-yl)carboxylic acid

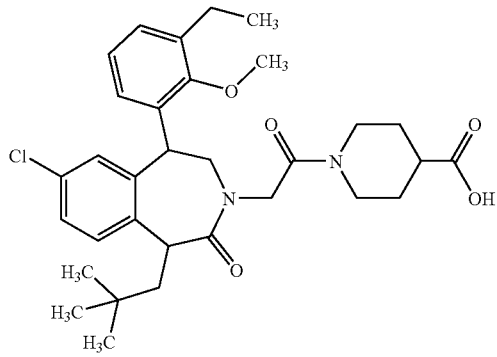

Example 45

(1-{2-[7-Chloro-5-(2,3-dihydrobenzo[1,4]dioxin-5-yl)-1-isobutyl-2-oxo-1,2,4,5-tetrahydrobenzo-[d]azepin-3-yl]-acetyl}piperidin-4-yl)carboxylic acid

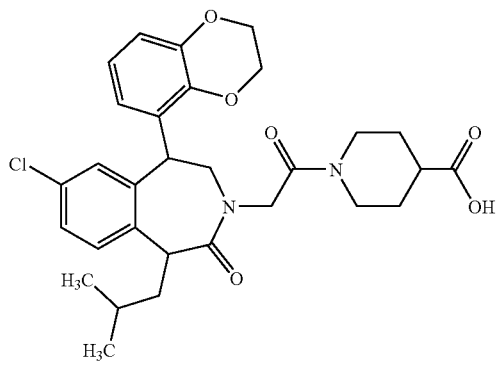

Example 46

(1-{2-[7-Chloro-1-isobutyl-5-(naphthalene-1-yl)-2-oxo-1,2,4,5-tetrahydrobenzo[d]azepin-3-yl]-acetyl}piperidin-4-yl)carboxylic acid

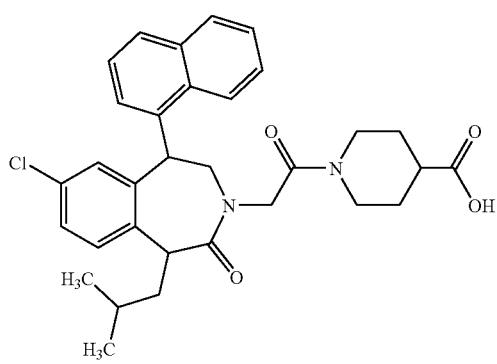

Example 47

(1-{2-[5-(2-Chloroprene)-1-isobutyl-7-methyl-2-oxo-1,2,4,5-tetrahydrobenzo[d]azepin-3-yl]-acetyl}piperidin-4-yl)carboxylic acid

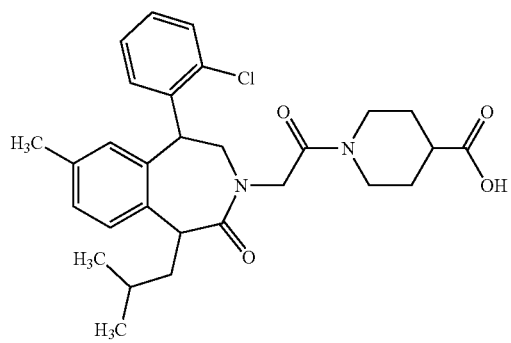

Example 48

(1-{2-[5-(2-Chloroprene)-1-isobutyl-2-oxo-7-trifluoromethyl-1,2,4,5-tetrahydrobenzo[d]azepin-3-yl]acetyl}piperidin-4-yl)carboxylic acid

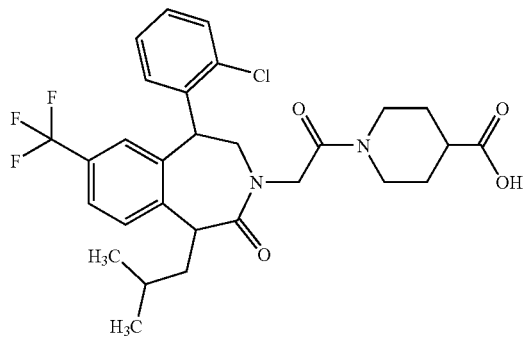

Example 49

(1-{2-[5-(2-Chloroprene)-1-(2,2-dimethylpropyl)-2-oxo-7-trifluoromethyl-1,2,4,5-tetrahydrobenzo[d]azepin-3-yl]acetyl}piperidin-4-yl)carboxylic acid

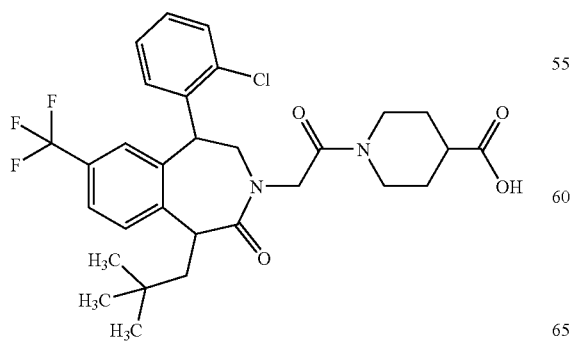

Example 50

(1-{2-[1-Isobutyl-5-(2-methoxyphenyl)-2-oxo-7-trifluoromethyl-1,2,4,5-tetrahydrobenzo[d]azepin-3-yl]acetyl}piperidin-4-yl)carboxylic acid

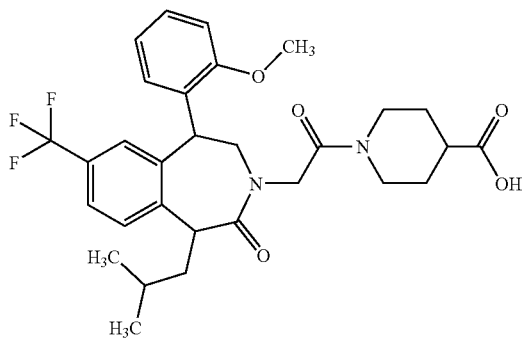

Example 51

(1-{2-[1-(2,2-Dimethylpropyl)-5-(2-methoxyphenyl)-2-oxo-7-trifluoromethyl-1,2,4,5-tetrahydrobenzo[d]azepin-3-yl]acetyl}piperidin-4-yl)carboxylic acid

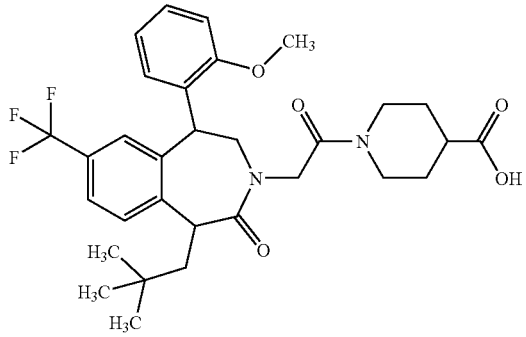

Example 52

(1-{2-[5-(2,3-Dimethoxyphenyl)-1-isobutyl-2-oxo-7-trifluoromethyl-1,2,4,5-tetrahydrobenzo[d]-azepin-3-yl]acetyl}piperidin-4-yl)carboxylic acid

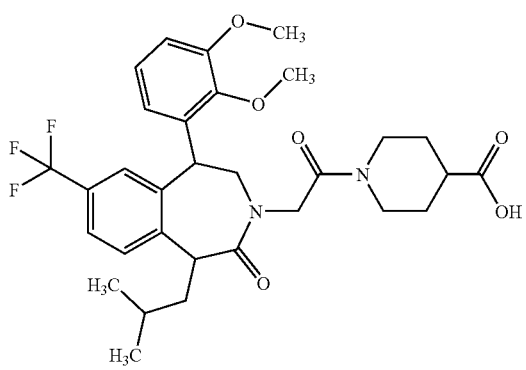

Example 53

(1-{2-[5-(2,3-Dimethoxyphenyl)-1-(2,2-dimethyl-propyl)-2-oxo-7-trifluoromethyl-1,2,4,5-tetrahydrobenzo[d]azepin-3-yl]acetyl}piperidin-4-yl)carboxylic acid

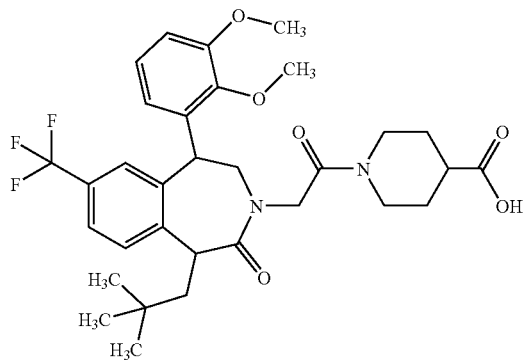

B. B. Assessment of the Pharmacological Activity

The pharmacological effect of the compounds according to the invention can be shown in the following assays:

1. Squalene Synthase Inhibition Assay
   a) Obtaining Microsomes:

Microsomes from rat livers are prepared as source of squalene synthase for the activity assay. The rat livers are comminuted and homogenized (Dounce homogenizer) in twice the volume of homogenization buffer [100 mM Tris/HCl, 0.2 M sucrose, 30 mM nicotinamide, 14 mM sodium fluoride, 5 mM dithiothreitol, 5 mM $MgCl_2$, protease inhibitor cocktail (from Sigma, Taufkirchen), pH 7.5]. The supernatant from a 10 000 g centrifugation is then centrifuged at 100 500 g. The pelleted microsomes are taken up in homogenization buffer, diluted to 10 mg/ml protein and stored at −80° C.

b) Squalene Synthase Activity Assay:

The conversion of trans,trans-[1-$^3$H]-farnesyl pyrophosphate into [$^3$H]-squalene by the microsomal squalene synthase takes place under the following reaction conditions: rat liver microsomes (protein content 65 μg/ml), 1 mM NADPH, 6 mM glutathione, 10% PBS, 10 mM sodium fluoride, 5 mM $MgCl_2$, pH 7.5. The compound to be tested in each case is dissolved in DMSO and added to the assay in a defined concentration. The reaction is started by adding farnesyl pyrophosphate (final concentration 5 μM) and 20 kBq/ml trans,trans-[1-$^3$H]-farnesyl pyrophosphate, and is incubated at 37° C. for 10 min. Subsequently, 100 μl of the reaction solution are mixed with 200 μl of chloroform, 200 μl of methanol and 60 μL of 5 N sodium hydroxide solution and adjusted to 2 mM squalene. After vigorous mixing and subsequent phase separation, an aliquot of the organic phase is transferred into scintillation fluid (Packard Ultima Gold LSC Cocktail) and the organically extractable radioactive compounds are quantified (LS 6500, from Beckman). The reduction in the radioactive signal is directly proportional to the inhibition of squalene synthase by the compound employed in each case.

The exemplary embodiments show $IC_{50}$ values of <20 μM in this assay.

2. Inhibition of Squalene and Cholesterol Synthesis in the Liver of Mice

Male NMRI mice are kept on normal rodent diet (NAFAG 3883) in metabolism cages. The light/dark cycle comprises 12 hours, from 06.00 to 18.00 and from 18.00 to 06.00. The animals are employed with a body weight of between 25 g and 40 g in groups of 8-10 animals in the experiments. Feed and drinking water are available to the animals ad libitum.

The substances are, according to their solubility, administered orally in aqueous tragacanth suspension (0.5%) or in Solutol HS15/saline solution (20:80) by gavage in a volume of 10 ml/kg of body weight or else injected subcutaneously in Solutol HS15/saline solution (20:80) or DMSO/saline solution (20:80). The corresponding control groups receive only the corresponding formulating agent without active substance. One or two hours after administration of the substance, the animals receive intraperitoneal injections of radiolabelled $^{14}$C-mevalonolactone. One or two hours after the $^{14}$C-mevalonolactone injection, or 2-4 hours after the administration of substance, the animals are sacrificed, the abdominal cavity is opened, and liver tissue is removed. Immediately after removal, the tissue is dried on the surface, weighed and homogenized in isopropanol. The further processing and extraction of the synthesized squalene and its secondary products takes place by a method of I. Duncan et al. (J. Chromatogr. 1979, 162), modified by H. Bischoff et al. (Atherosclerosis 1997, 135).

The extracted lipid fraction is taken up in 1 ml of isopropanol, transferred into scintillation vials, made up with 15 ml of Ultima Gold® scintillation fluid (Packard) and counted in a liquid scintillation counter (Beckmann Coulter LS 6500).

After calculation of the specific $^{14}$C activity of the lipid fraction (dpm/g of liver tissue), the rate of synthesis of the radiolabelled $^{14}$C squalene and of the $^{14}$C secondary metabolites of the animals treated with active substance is compared with the rate of synthesis of the radiolabelled $^{14}$C squalene and of the $^{14}$C secondary metabolites of the control animals treated only with formulating agent. A reduction in the rate of synthesis by ≧30% compared with the rate of synthesis for the control animals (=100%) is regarded as pharmacologically active if the statistical assessment by Student's t test results in a p value of <0.05.

3. Inhibition of Squalene and Cholesterol Synthesis in the Liver of Rats

Male Wistar rats are kept on normal rodent diet (NAFAG 3883) in Makrolon® type III cages. The light/dark cycle comprises 12 hours, from 06.00 to 18.00 and from 18.00 to 06.00. The animals are employed with a body weight of between 150 g and 200 g in groups of 6-8 animals in the experiments. The feed is withdrawn from the animals 18-22 hours before the start of the experiment; drinking water is available ad libitum up to the end of the experiment.

The substances are, according to their solubility, administered orally in aqueous tragacanth suspension (0.5%) or in Solutol HS15/saline solution (20:80) by gavage in a volume of 10 ml/kg of body weight or else injected subcutaneously in Solutol HS15/saline solution (20:80) or DMSO/saline solution (20:80). The corresponding control groups receive only the corresponding formulating agent without active substance. One or two hours after administration of the substance, the animals receive intraperitoneal injections of radiolabelled $^{14}$C-mevalonolactone. One or two hours after the $^{14}$C-mevalonolactone injection, or 2-4 hours after the administration of substance, the animals are sacrificed, the abdominal cavity is opened, and liver tissue is removed. Immediately after removal, the tissue is dried on the surface, weighed and homogenized in isopropanol. The further processing and extraction of the synthesized squalene and its secondary products takes place by a method of I. Duncan et al. (*J. Chromatogr.* 1979, 162), modified by H. Bischoffet al. (*Atherosclerosis* 1997, 135).

The extracted lipid fraction is taken up in 1 ml of isopropanol, transferred into scintillation vials, made up with 15 ml of Ultima Gold® scintillation fluid (Packard) and counted in a liquid scintillation counter (Beckmann Coulter LS 6500).

After calculation of the specific $^{14}C$ activity of the lipid fraction (dpm/g of liver tissue), the rate of synthesis of the radiolabelled $^{14}C$ squalene and of the $^{14}C$ secondary metabolites of the animals treated with active substance is compared with the rate of synthesis of the radiolabelled $^{14}C$ squalene and of the $^{14}C$ secondary metabolites of the control animals treated only with formulating agent. A reduction in the rate of synthesis by $\geq 30\%$ compared with the rate of synthesis for the control animals ($=100\%$) is regarded as pharmacologically active if the statistical assessment by Student's t test results in a p value of <0.05.

C. Exemplary Embodiments of Pharmaceutical Compositions

The compounds according to the invention can be converted into pharmaceutical preparations in the following ways:

Tablet:
  Composition:
  100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.
  Tablet weight 212 mg, diameter 8 mm, radius of curvature 12 mm.
  Production:
  A mixture of compound according to the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension Which Can Be Administered Orally:
  Composition:
  1000 mg of the compound according to the invention, 1000 mg of ethanol (96%), 400 mg of Rhodigel® (xanthan gum from FMC, Pennsylvania, USA) and 99 g of water.
  10 ml of oral suspension correspond to a single dose of 100 mg of the compound according to the invention.
  Production:
  The Rhodigel is suspended in ethanol, and the compound according to the invention is added to the suspension. The water is added while stirring. The mixture is stirred for about 6 h until the swelling of the Rhodigel is complete.

Solution which Can Be Administered Orally:
  Composition:
  500 mg of the compound according to the invention, 2.5 g of polysorbate and 97 g of polyethylene glycol 400. 20 g of oral solution correspond to a single dose of 100 mg of the compound according to the invention.
  Production:
  The compound according to the invention is suspended in the mixture of polyethylene glycol and polysorbate with stirring. The stirring process is continued until the compound according to the invention has completely dissolved.

i.v. Solution:
  The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of the formula (I)

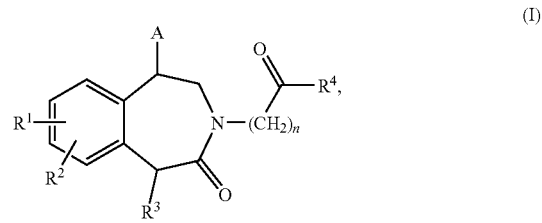

in which
  A is $(C_6-C_{10})$-aryl or 5- to 10-membered heteroaryl, each of which may be substituted up to three times, identically or differently, by substituents selected from the group consisting of halogen, cyano, nitro, trifluoromethyl, trifluoromethoxy, $(C_1-C_6)$-alkyl, $(C_2-C_6)$-alkynyl and $(C_1-C_6)$-alkoxy,
  or
  is a group of the formula

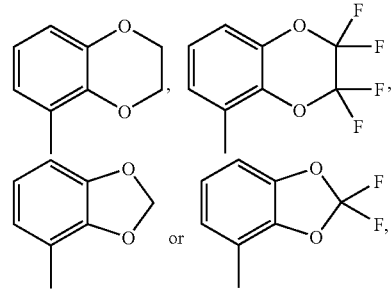

n is the number 1, 2 or 3,
  $R^1$ and $R^2$ are identical or different and are independently of one another hydrogen, halogen, cyano, nitro, trifluoromethyl, trifluoromethoxy, $(C_1-C_6)$-alkyl or $(C_1-C_6)$-alkoxy,
  $R_3$ is $(C_1-C_8)$-alkyl, $(C_2-C_8)$-alkenyl or $(C_2-C_8)$-alkynyl, each of which may be substituted by phenyl, $(C_3-C_8)$-cycloalkyl, hydroxy, $(C_1-C_6)$-alkoxy, $(C_1-C_6)$-acyloxy or amino,
  and
  $R_4$ is a group of the formula $—OR^7$ or $—NR^8R^9$, in which
    $R_7$ is hydrogen or $(C_1-C_6)$-alkyl,
    $R_8$ and $R_9$ are identical or different and are independently of one another hydrogen, $(C_1-C_6)$-alkyl or $(C_3-C_8)$-cycloalkyl, each of which may be substituted by substituents selected from the group consisting of carboxyl, $(C_1-C_6)$-alkoxycarbonyl, aminocarbonyl, and mono- and di-$(C_1-C_6)$-alkylaminocarbonyl,
    or
    $R^8$ and $R^9$ form together with the nitrogen atom to which they are bonded a 4- to 8-membered heterocycle which may comprise a further ring member selected from the series N—$R^{10}$, O, S, SO and $SO_2$ and may be substituted by substituents selected from the group consisting of hydroxy, oxo, amino, ($C_1$-$C_6$)-alkyl, carboxyl, ($C_1$-$C_6$)-alkoxycarbonyl, aminocarbonyl, and mono- and di-($C_1$-$C_6$)-alkylaminocarbonyl, in which
($C_1$-$C_6$)-alkyl in turn may be substituted by substituents selected from the group consisting of hydroxy, amino, carboxyl, ($C_1$-$C_6$)-alkoxycarbonyl, aminocarbonyl, and mono- and di-($C_1$-$C_6$)-alkylaminocarbonyl,
and
$R_{10}$ is hydrogen, ($C_1$-$C_4$)-alkyl, ($C_1$-$C_4$)-acyl or ($C_1$-$C_4$)-alkoxycarbonyl,
or a salt thereof.

2. The compound of the formula (I) according to claim 1, in which
A is phenyl, naphthyl or pyridyl, each of which may be substituted up to twice, identically or differently, by substituents selected from the group consisting of fluorine, chlorine, bromine, cyano, trifluoromethyl, trifluoromethoxy, ($C_1$-$C_4$)-alkyl, ($C_2$-$C_4$)-alkynyl and ($C_1$-$C_4$)-alkoxy,
or
is a group of the formula

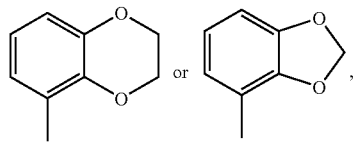

n is the number 1, 2 or 3,
$R_1$ is hydrogen, fluorine, chlorine, cyano, trifluoromethyl, trifluoromethoxy, ($C_1$-$C_4$)-alkyl or ($C_1$-$C_4$)-alkoxy,
R2 is hydrogen,
R3 is ($C_1$-$C_6$)-alkyl or ($C_2$-$C_6$)-alkenyl, each of which may be substituted by phenyl, ($C_3$-$C_6$)-cycloalkyl or hydroxy,
and
$R_4$ is a group of the formula —$OR^7$ or —$NR^8R^9$ in which
$R^7$ is hydrogen,
$R^8$ and $R^9$ are identical or different and are independently of one another hydrogen, ($C_1$-$C_6$)-alkyl or ($C_3$-$C_6$)-cycloalkyl, each of which may be substituted by substituents selected from the group consisting of carboxyl, ($C_1$-$C_4$)-alkoxycarbonyl, aminocarbonyl, and mono- and di-($C_1$-$C_4$)-alkylaminocarbonyl,
or
$R^8$ and $R^9$ form together with the nitrogen atom to which they are bonded a 5- to 7-membered heterocycle which may comprise a further ring member selected from the series N—$R^{10}$ and O and may be substituted by substituents selected from the group consisting of hydroxy, oxo, amino, ($C_1$-$C_4$)-alkyl, carboxyl, ($C_1$-$C_4$)-alkoxycarbonyl, aminocarbonyl, and mono- and di-($C_1$-$C_4$)-alkylaminocarbonyl, in which
($C_1$-$C_4$)-alkyl in turn may be substituted by substituents selected from the group consisting of hydroxy, amino, carboxyl, ($C_1$-$C_4$)-alkoxycarbonyl, aminocarbonyl, and mono- and di-($C_1$-$C_4$-alkylaminocarbonyl,
and
$R^{10}$ is hydrogen, ($C_1$-$C_4$)-alkyl, ($C_1$-$C_4$)-acyl or ($C_1$-$C_4$)-alkoxycarbonyl, or a salt thereof.

3. The compound of the formula (I) according to claim 1 or 2, in which
A is phenyl which may be substituted once or twice, identically or differently, by fluorine, chlorine, bromine, methyl, ethyl, ethynyl or methoxy, or is naphthyl or is a group of the formula

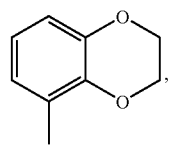

n is the number 1,
$R^1$ is hydrogen, chlorine, methyl or trifluoromethyl,
$R^2$ is hydrogen,
$R^3$ is ($C_1$-$C_6$)-alkyl, ($C_2$-$C_6$)-alkenyl or is benzyl,
and
$R^4$ is a group of the formula —$OR^7$ or —$NR^8R^9$ in which
$R_7$ is hydrogen,
$R^8$ and $R^9$ are identical or different and are independently of one another hydrogen or ($C_1$-$C_6$)-alkyl which may be substituted by carboxyl or ($C_1$-$C_4$)-alkoxycarbonyl,
or
$R^8$ and $R^9$ form together with the nitrogen atom to which they are bonded a 5- to 6-membered heterocycle which may comprise a further ring member selected from the series N—$R^{10}$ and O and may be substituted by substituents selected from the group consisting of hydroxy, oxo, amino, ($C_1$-$C_4$)-alkyl, carboxyl, ($C_1$-$C_4$)-alkoxycarbonyl, aminocarbonyl, and mono- and di-($C_1$-$C_4$)-alkylarninocarbonyl, in which
($C_1$-$C_4$)-alkyl in turn may be substituted by substituents selected from the group consisting of hydroxy, amino, carboxyl, ($C_1$-$C_4$)-alkoxycarbonyl, aminocarbonyl, and mono- and di-($C_1$-$C_4$)-alkylaminocarbonyl,
$R^{10}$ is hydrogen, ($C_1$-$C_4$)-alkyl or ($C_1$-$C_4$)-acyl,
or a salt thereof.

4. A compound of the formula (I-A)

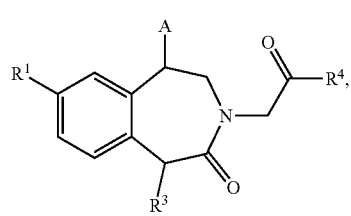

(I-A)

in which
A is phenyl which may be substituted once or twice, identically or differently, by fluorine, chlorine, bromine, methyl, ethynyl or methoxy, or is a group of the formula

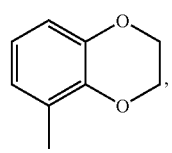

$R^1$ is chlorine, methyl or trifluoromethyl, $R^3$ is $(C_1-C_6)$-alkyl or $(C_2-C_6)$-alkenyl, and $R^4$ is a group of the formula —$OR^7$ or —$NR^8R^9$ in which $R^7$ is hydrogen, $R^8$ and $R^9$ are identical or different and are independently of one another hydrogen or $(C_1-C_6)$-alkyl which may be substituted by carboxyl or $(C_1-C_4)$-alkoxycarbonyl, or $R^8$ and $R^9$ form together with the nitrogen atom to which they are bonded a 5- to 6-membered heterocycle which may comprise a further ring member selected from the series N—$R^{10}$ and O and may be substituted by substituents selected from the group consisting of hydroxy, oxo, amino, $(C_1-C_4)$-alkyl, carboxyl, $(C_1-C_4)$-alkoxycarbonyl, aminocarbonyl, and mono- and di-$(C_1-C_4)$-alkylaminocarbonyl, in which $(C_1-C_4)$-alkyl in turn may be substituted by substituents selected from the group consisting of hydroxy, amino, carboxyl, $(C_1-C_4)$-alkoxycarbonyl, aminocarbonyl, and mono- and di-$(C_1-C_4)$-alkylaminocarbonyl, and $R^{10}$ is hydrogen, $(C_1-C_4)$-alkyl or $(C_1-C_4)$-acyl, or a salt thereof.

5. A pharmaceutical composition comprising a compound as defined in claim 1 in combination with a further active ingredient selected from the group consisting of cholesterol-lowering statins, cholesterol absorption inhibitors, HDL-elevating or triglyceride-lowering and/or apolipoprotein B-lowering substances, oxidation inhibitors and compounds having antiinflammatory activity.

6. A pharmaceutical composition comprising a compound as defined in claim 1 in combination with an inert, nontoxic, pharmaceutically suitable excipient.

* * * * *